US012735706B2

(12) United States Patent
Maguire et al.

(10) Patent No.: US 12,735,706 B2
(45) Date of Patent: Sep. 15, 2026

(54) ABCD1 FOR TREATMENT OF NEURODISORDERS

(71) Applicant: The General Hospital Corporation, Boston, MA (US)

(72) Inventors: Casey A. Maguire, Arlington, MA (US); Florian Eichler, Cambridge, MA (US); Yi Gong, Malden, MA (US)

(73) Assignee: The General Hospital Corporation, Boston, MA (US)

( * ) Notice: Subject to any disclaimer, the term of this patent is extended or adjusted under 35 U.S.C. 154(b) by 139 days.

(21) Appl. No.: 18/295,566

(22) Filed: Apr. 4, 2023

(65) Prior Publication Data

US 2023/0365967 A1 Nov. 16, 2023

Related U.S. Application Data

(63) Continuation of application No. 15/773,337, filed as application No. PCT/US2016/060375 on Nov. 3, 2016, now abandoned.

(60) Provisional application No. 62/300,691, filed on Feb. 26, 2016, provisional application No. 62/251,208, filed on Nov. 5, 2015.

(51) Int. Cl.

| | |
|---|---|
| ***C12N 15/85*** | (2006.01) |
| ***A61K 9/00*** | (2006.01) |
| ***A61K 48/00*** | (2006.01) |
| ***A61P 25/00*** | (2006.01) |
| ***A61P 25/28*** | (2006.01) |
| ***C12N 15/113*** | (2010.01) |
| ***C12N 15/86*** | (2006.01) |

(52) U.S. Cl.

CPC .......... *C12N 15/113* (2013.01); *A61K 9/0004* (2013.01); *A61K 9/0085* (2013.01); *A61K 48/005* (2013.01); *A61K 48/0075* (2013.01); *A61P 25/28* (2018.01); *C12N 15/86* (2013.01); *A61K 48/00* (2013.01); *C12N 2310/14* (2013.01); *C12N 2750/14141* (2013.01); *C12N 2750/14143* (2013.01); *C12N 2750/14152* (2013.01)

(58) Field of Classification Search

CPC .... C12N 15/85; C12N 15/86; C12N 15/8645; C12N 15/8673; C12N 15/113; C12N 2310/14; C12N 2750/14141; C12N 2750/14143; C12N 2750/14152; A61K 48/00; A61P 25/00

See application file for complete search history.

(56) References Cited

U.S. PATENT DOCUMENTS

| | | | | |
|---|---|---|---|---|
| 6,013,769 | A | 1/2000 | Mandel | |
| 6,225,525 | B1 | 5/2001 | Leung et al. | |
| 7,192,579 | B2 | 3/2007 | Allikmets et al. | |
| 2005/0032219 | A1* | 2/2005 | Aubourg | C12N 15/86 435/456 |
| 2012/0331576 | A1* | 12/2012 | Brass | C12N 7/00 435/235.1 |
| 2013/0004471 | A1 | 1/2013 | Denaro et al. | |
| 2013/0202559 | A1 | 8/2013 | Skog et al. | |
| 2014/0010861 | A1 | 1/2014 | Bancel | |
| 2018/0320176 | A1* | 11/2018 | Maguire | A61K 48/0075 |

FOREIGN PATENT DOCUMENTS

| | | |
|---|---|---|
| CN | 103717240 | 4/2014 |
| JP | 2014-519335 A | 8/2014 |
| WO | WO 2012/170911 | 12/2012 |
| WO | WO 2014/015318 | 1/2014 |
| WO | WO 2014/186579 | 11/2014 |
| WO | WO 2015/060722 | 4/2015 |
| WO | WO 2015/114365 | 8/2015 |

OTHER PUBLICATIONS www.calculator.net/exponent-calculator.html; last visited Feb. 4, 2025.*

Fakler et al, Short Antisense Oligonucleotide-mediated Inhibition Is Strongly Dependent on Oligo Length and Concentration but Almost Independent of Location of the Target Sequence, J. Biol. Chem. 269 (23): 16187-16194, 1994.*

Ki et al, The optimal concentration of siRNA for gene silencing in primary cultured astrocytes and microglial cells of rats, Korean J. Anethsiol. 59(6): 403-410, 2010.*

Strobel et al, Riboswitch-mediated Attenuation of Transgene Cytotoxicity Increases Adeno-associated Virus Vector Yields in HEK-293 Cells, Molecular Therapy 23(10): 1582-1591, available online Jul. 28, 2015.*

Manfredsson et al (AAV9: a potential blood-brain barrier buster, Molecular Therapy 17(3): 403-405, 2009).*

Singh et al, Silencing of Abcd1 and Abcd2 genes sensitizes astrocytes for inflammation: implication for X-adrenoleukodystrophy, J. Lipid Research 50: 135-147, 2009.*

Aalto et al, Large-scale production of dsRNA and siRNA pools for RNA interference utilizing bacteriophage f6 RNA-dependent RNA polymerase, RNA 13: 422-429, 2007.*

Hannus et al, siPools: highly complex but accurately defined siRNA pools eliminate off-target effects, Nucleic Acids Res. 42(12): 8049-8061, 2014.*

GenBank NM_000033.3, human ABCD1, 2020.*

Kim et al, Development of a cell-defined siRNA microarray for analysis of gene function in human bone marrow stromal cells, Stem Cells Research 16(2): 365-376; available online Feb. 10, 2016.*

'www.ncbi.nlm.nih.gov' [online]. "X-Linked Adrenoleukodystrophy," dated Mar. 26, 1999, last updated on Feb. 15, 2018 [retrieved on Oct. 3, 2018]. Retrieved from the Internet: URL <https://www.ncbi.nlm.nih.gov/books/NBK1315/>. 19 pages.

(Continued)

*Primary Examiner* — Kevin K Hill
(74) *Attorney, Agent, or Firm* — Fish & Richardson P.C.

(57) ABSTRACT

Methods of the invention encompass delivery of nucleic acid sequences encoding ABCD1 for the treatment of X-linked Adrenoleukodystrophy (X-ALD), e.g., for Adrenomyeloneuropathy (AMN).

11 Claims, 8 Drawing Sheets

Specification includes a Sequence Listing.

(56) References Cited

OTHER PUBLICATIONS

Aubourg and Chaussain, "Adrenoleukodystrophy: The Most Frequent Genetic Cause of Addison's Disease," Horm Res, 2003, 59 Suppl 1:104-5.

Barton, "Viral expression of insulin-like growth factor-I isoforms promotes different responses in skeletal muscle," J Appl Physiol., 2006, 100:1778-1784.

Broekman et al, "Adeno-Associated Virus Vectors Serotyped With AAV8 CAPSID Are More Efficient Than AAV-1 or -2 Serotypes for Widespread Gene Delivery to the Neonatal Mouse Brain," Neurosci. 138: 501-510, 2006.

Chu et al., "Intrathecal baclofen in X-linked adrenoleukodystrophy," Pediatric Neurology, 2001, 24(2):156-158.

CN Office Action in Chinese Appln. No. 201680077741.7, dated Jun. 3, 2020, 12 pages (with English translation).

D'Costa et al., "Practical utilization of recombinant AAV vector reference standards: focus on vector genomes titration by free ITR qPCR," Mol. Ther.—Meth. Clin. Dev., 2016, 5:16019.

Decision to Grant in European Appln. No. 16862990.5, dated Feb. 10, 2022, 2 pages.

EP Office Action in European Appln. No. 16862990.5, dated Apr. 28, 2020, 6 pages.

Extended European Search Report in Application No. 16892990.5, dated Apr. 16, 2019, 10 pages.

Foust et al., "Intravascular AAV9 preferentially targets neonatal-neurons and adult-astrocytes in CNS," Nat. Biotechnol., Jan. 2009, 27(1):59-65.

Furlan et al, "Cytokine Gene Delivery into the Central Nervous System Using Intrathecally Injected Nonreplicative Viral Vectors," Methods Mol. Biol., 2003, 215:279-289.

GenBank Accession No. NM_000033.3, "*Homo sapiens* ATP binding cassette subfamily D member 1 (ABCD1), mRNA," Apr. 28, 2020, 5 page.

Gong et al., "Adenoassociated Virus Serotype 9-medialed Gene Therapy for X-Linked Adrenoleukodystrophy," Molecular Therapy, May 2015, 23: 824-834.

Gray et al., "Viral vectors and delivery strategies for CNS gene therapy," Ther Deliv, Oct. 2010, 1: 517-534.

International Preliminary Report on Patentability in International Application No. PCT/US2016/060375, dated May 8, 2018, 7 pages.

International Search report and Written Opinion in International Application No. PCT/US2016/060375, mailed on Feb. 27, 2017, 12 pages.

Iwamoto et al., "Global diffuse distribution in the brain and efficient gene delivery to the dorsal root ganglia by intrathecal injection of adeno-associated viral vector serotype 1," J. Gene Medicine, 2009, 11: 498-505.

JP Office Action in Japanese Application No. 2018-543041, dated Oct. 27, 2020, 10 pages (with English translation).

JP Search Report in Japanese Application No. 2018-543041, dated Sep. 30, 2020, 35 pages (with English translation).

Katz et al., "Gene Therapy in Cardiac Surgery: Clinical Trials, Challenges, and Perspectives," Ann Thorac Surg, Jun. 2016, 101: 2407-2416.

Kohlschutter et al., "Novel Cytotoxic Vectors Based on Adeno-Associated Virus," Toxins, Dec. 2010, 2: 2754-2738.

Maguire et al, "Preventing Growth of Brain Tumors by Creating a Cone of Resistance," Mol. Therapy., 2008, 16(10): 1695-1702.

Mastroeni et al., "Insulin-like growth factor-1 and neurotrophin-3 gene therapy prevents motor decline in an X-linked adrenoleukodystrophy mouse model," Ann. Neurol., Mar. 2009, 66:117-122.

Matalon et al, "Adeno-associated virus-mediated aspartoacylase gene transfer to the brain of knockout mouse for canavan disease," Molecular Therapy, 2003, 7(5):580-587.

Notice of Allowance in Japanese Appln. No. 2018-543041, dated Jan. 28, 2022, 5 pages (with English translation).

Office Action in Australian Appln. No. 2016349381, dated Jun. 1, 2022, 4 pages.

Office Action in Indian Appln. No. 201817019964, dated Mar. 10, 2022, 7 pages.

Office Action in Mexican Appln. No. MX/a/2018/005689, dated May 3, 2022, 17 pages (with English machine translation).

Pujol et al., "Late onset neurological phenotype of the X-ALD gene inactivation in mice: a mouse model for adrenomyeloneuropathy," Hum Mol Genet, 2002, 11:499-505.

Reid et al., "Improved packaging efficiency for ocular applications of AAV vectors through inclusion of miRNA recognition sequences," ARVO Annual Meeting Abstract, Jun. 2015, 2 pages.

Rohr et al., "Fast and reliable titration of recombinant adeno-associated virus type-2 using quantitative real-time PCR," J. Virol. Meth., Oct. 2002, 106(1):81-88.

RU Office Action in Russian Appln. No. 2018120484, dated Mar. 10, 2020, 18 pages (with English translation).

Ruzo et al, "Correction of Pathological Accumulation of Glycosaminoglycans in Central Nervous System and Peripheral Tissues of MPSIIIA Mice Through Systemic AAV9 Gene Transfer," Human Gene Therapy, 2012, 23:1237-1246.

SG Office Action in Singapore Appln. No. 11201803353P, dated Jun. 15, 2020, 6 pages.

SG Search Report in Singapore Appln. No. 11201803353P, dated Jul. 8, 2019, 10 pages.

Simonato et al., "Progress in gene therapy for neurological disorders," Nature Reviews Neurology, 2013, 9: 277-291.

Singh et al., "Silencing of Abcd1 and Abcd2 genes sensitizes astrocytes for inflammation: implication for X-adrenoleukodystrophy," J Lipid Res. Jan. 2009, 50(1):135-147.

Steinberg et al., "Investigational Methods for Peroxisomal Disorders," Curr Protoc Hum Genet, Chapter 17:Unit 17.6, 2008, 23 pages.

Strobel et al., "Abstract #: 678. Increasing AAV Vector Yield by Riboswitch-Mediated Attenuation of Toxic Transgene Effects in HEK-293 Producer Cells," Molecular Therapy, 2015, 23: S269-S270.

Wang et al., "An shRNA silencing a non-toxic transgene reduces nutrient consumption and increases production of adenoviral vectors in a novel packaging cell," Journal of Cellular Physiology, May 2009, 219: 365-371.

Wikipedia.com [online], "List of organs of the human body," [retrieved on Jan. 22, 2020], retrieved from: URL <https://en.wikipedia.org/w/index.php?title=List of organs of the human body &oldid=932512135>; last visited Jan. 22, 2020, 5 pages.

Yamada et al., "Therapeutic effects of normal cells on ABCD1 deficient cells in vitro and hematopoietic cell transplantation in the X-ALD mouse model," J. Neurol. Sci., Mar. 2004, 218:91-97.

Gray et al., "Global CNS Gene Delivery and Evasion of Anti-AAV Neutralizing Antibodies by Intrathecal AAV Administration in Non-Human Primates," HHS Public Access Author Manuscript, doi: 10.1038/gt.2012.101, published online Oct. 1, 2013; published in final edited form as: Gene Therapy, Apr. 2013, 20(4):450-459, 22 pages.

Office Action in Canadian Appln. No. 3003747, dated Aug. 22, 2024, 4 pages.

Engelen et al., "X-linked adrenoleukodystrophy (X-ALD): clinical presentation and guidelines for diagnosis, follow-up and management," Orphanet Journal of Rare Diseases, Aug. 2012, 7:51, 14 pages.

Schuster et al, "Biodistribution of adeno-associated virus serotype 9 (AAV9) vector after intrathecal and intravenous delivery in mouse," Frontiers in Neuroanatomy, Jun. 2014, 8:42, 14 pages.

* cited by examiner

ABCD1 FOR TREATMENT OF NEURODISORDERS

RELATED APPLICATIONS

This application is a continuation of U.S. patent application Ser. No. 15/773,337, filed May 3, 2018, which is a § 371 National Stage Application of PCT/US2016/060375, filed Nov. 3, 2016, which claims the benefit of U.S. Provisional Application No. 62/300,691, filed Feb. 26, 2016, and U.S. Provisional Application No. 62/251,208, filed Nov. 5, 2015. The entire disclosures of the aforementioned applications are incorporated herein by reference.

FEDERALLY SPONSORED RESEARCH OR DEVELOPMENT

This invention was made with government support under Grant Nos. NS081374 and NS072446 awarded by the National Institutes of Health. The government has certain rights in the invention.

SEQUENCE LISTING

This application contains a Sequence Listing that has been submitted electronically as an XML file named "40978-0022003_SL_ST26.XML." The XML file, created on Apr. 4, 2023, is 45,068 bytes in size. The material in the XML file is hereby incorporated by reference in its entirety.

BACKGROUND OF THE INVENTION

X-linked adrenoleukodystrophy (X-ALD), a progressive genetic disorder, is caused by mutations in the ABCD1 gene, which encodes a peroxisomal ATP-binding cassette transporter (ABCD1) responsible for transport of CoA-activated very long-chain fatty acids (VLCFA) into the peroxisome for degradation leading to the accumulation of high levels of saturated, very long chain fatty acids (VLCFA) in plasma and tissues of the brain and adrenal cortex. Symptoms can begin in childhood or adulthood. Adult ALD patients typically develop adrenomyeloneuropathy (AMN), a debilitating neurological disorder, in their twenties (Engelen et al., Orphanet J Rare Dis. 2012; 7: 51). The Abcd1$^{-/-}$ mouse develops a phenotype similar to AMN, manifesting spinal cord axon degeneration as well as peripheral neuropathy due to affected dorsal root ganglion neurons (DRGs) (Pujol et al., Hum Mol Genet. 2002; 11:499-505). Transduction of central nervous system cells in vitro and in vivo using recombinant adeno-associated virus serotype 9 (rAAV9) vector for delivery of the human ABCD1 gene was previously reported. Unfortunately, intravenous delivery in young mice is associated with cardiac toxicity due to transgene overexpression. Delivery systems that provide non-toxic levels of ABCD1 in patients suffering from X-ALD or AMN would be highly desirable.

SUMMARY OF THE INVENTION

Other features and advantages of the invention will be apparent from the Detailed Description, and from the claims. Thus, other aspects of the invention are described in the following disclosure and are within the ambit of the invention.

In one aspect, the invention provides a method of increasing adeno-associated Virus 9 (AAV9) vector titers in transfected producer cells grown in culture, said method comprising the steps of i) incubating a nucleic acid sequence that is complementary to an mRNA encoding ATP binding cassette subfamily D member 1 (ABCD1) with the cells and ii) transfecting an AAV9 vector comprising a nucleotide sequence encoding ABCD1 into the cells (AAV9-ABCD1 vector), wherein the amount of ABCD1 mRNA expressed from the AAV9 vector is decreased, thereby increasing AAV9-ABCD1 vector yield in cell lysate and/or media by about 1 fold to about 50 fold compared to a reference standard.

In one embodiment, the nucleic acid sequence that is complementary to an mRNA encoding ABCD1 is an interfering RNA.

In another embodiment, the interfering RNA is an shRNA or siRNA.

In yet another embodiment, the siRNA comprises SEQ ID NO. 4, SEQ ID NO. 5, SEQ ID NO. 6, SEQ ID NO. 7 or a combination thereof.

In yet another embodiment, the reference standard comprises AAV9-ABCD1 vector yield in cell lysate and/or media from producer cells that were not incubated with a nucleic acid sequence that is complementary to an mRNA encoding ABCD1.

In yet another aspect, the invention provides a method of treating X-linked adrenoleukodystrophy (X-ALD) in a subject in need thereof comprising administering to the subject a composition comprising purified AAV9-ABCD1 vector obtained from the producer cells having increased AAV9 vector titers compared to a reference standard.

In one embodiment, the composition comprising purified AAV9-ABCD1 vector is administered to the subject by intrathecal administration.

In yet another aspect, the invention provides a method of treating X-linked adrenoleukodystrophy (X-ALD) in a subject in need thereof comprising administering to the subject an adeno-associated Virus (AAV) vector encoding an ATP binding cassette subfamily D member 1 (ABCD1), wherein said vector is administered to the subject by intrathecal administration.

In one embodiment, the intrathecal administration is mediated by an osmotic pump.

In another embodiment, the dose of vector is $0.5\times10^{11}$ GC.

In yet another embodiment, the AAV is AAV9.

In yet another aspect, the invention provides a method of providing ATP binding cassette subfamily D member 1 (ABCD1) to a subject having X-linked adrenoleukodystrophy (X-ALD) comprising administering to the subject a vector encoding ABCD1, wherein said vector is administered to the subject by intrathecal administration, and wherein ABCD1 expression from said vector in the central nervous system is less than ABCD1 expression from said vector in peripheral organs.

In one embodiment, the intrathecal administration is mediated by an osmotic pump.

In another embodiment, the dose of vector is about $1\times10^{13}$ GC to about $10\times10^{13}$ GC.

In yet another embodiment, the vector is an adeno-associated virus (AAV) vector.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

BRIEF DESCRIPTION OF THE DRAWINGS

The following Detailed Description, given by way of example, but not intended to limit the invention to certain embodiments described, may be understood in conjunction with the accompanying figures, incorporated herein by reference.

DETAILED DESCRIPTION OF THE INVENTION

Definitions

Figure 1:
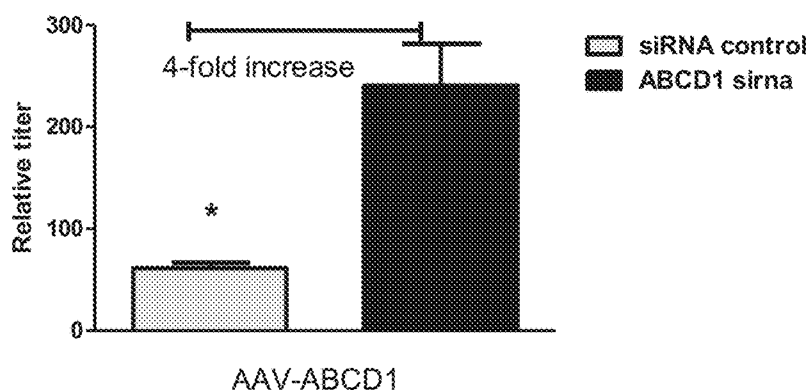
FIG. 1 depicts improved AAV9-ABCD1 vector titers from transfected 293T cells incubated with siRNA specific for ABCD1 mRNA.

Unless otherwise defined, all technical and scientific terms used herein have the same meaning as commonly understood by one of ordinary skill in the art to which this invention belongs. In case of conflict, the present application, including definitions will control.

A "subject" is a vertebrate, including any member of the class mammalia, including humans, domestic and farm animals, and zoo, sports or pet animals, such as mouse, rabbit, pig, sheep, goat, cattle and higher primates.

As used herein, the terms "treat," "treating," "treatment," and the like refer to reducing or ameliorating X-ALD, e.g., adrenomyeloneuropathy (AMN), and/or symptoms associated therewith. It will be appreciated that, although not precluded, treating X-ALD or AMN does not require that the disorder, condition or symptoms associated therewith be completely eliminated.

Unless specifically stated or clear from context, as used herein, the term "about" is understood as within a range of normal tolerance in the art, for example within 2 standard deviations of the mean. "About" is understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used herein "a decrease in expression" refers to an amount of ABCD1 gene expression or protein expression in peripheral organs of a subject that is at least about 0.05 fold less (for example 0.1, 0.2, 0.3, 0.4, 0.5, 1, 5, 10, 25, 50, 100, 1000, 10,000-fold or more less) than the amount of ABCD1 gene expression or protein expression in the central nervous system of a subject having been administered a vector encoding ABCD1 according to the methods described herein. "Decreased" as it refers to ABCD1 gene expression or protein expression in peripheral organs of a subject also means at least about 5% less (for example 5, 6, 7, 8, 9, 10, 15, 20, 25, 30, 35, 40, 45, 50, 55, 60, 65, 70, 75, 80, 85, 90, 95, 99 or 100%) than the amount of ABCD1 gene expression or protein expression in the central nervous system of a subject having been administered a vector encoding ABCD1 according to the methods described herein. Amounts can be measured according to standard methods known in the art for determining amounts of gene expression or protein expression.

As used herein "an increase in vector titers" refers to an amount of titer from producer cells transfected with a vector encoding ABCD1 that is at least about 0.05 fold more (for example 0.1, 0.2, 0.3, 0.4, 0.5, 1, 5, 10, 25, 50, 100, 1000, 10,000-fold or more) than the amount of titer from producer cells that were not incubated with a nucleic acid sequence that is complementary to an mRNA encoding ABCD1 according to the methods described herein. "Increased" as it refers to an amount of titer (concentration of AAV vector, often described in genome copies per milliliter) from producer cells transfected with a vector encoding ABCD1 also means at least about 5% more (for example 5, 6, 7, 8, 9, 10, 15, 20, 25, 30, 35, 40, 45, 50, 55, 60, 65, 70, 75, 80, 85, 90, 95, 99 or 100%) than the amount of titer from producer cells that were not incubated with a nucleic acid sequence that is complementary to an mRNA encoding ABCD1 according to the methods described herein. Amounts can be measured according to standard methods known in the art for determining amounts of AAV genomes, transgene expression, or protein expression.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

As used herein, the term "reference level" refers to the level of titer in a known sample against which another test sample is compared. A reference level can be obtained, for example, from producer cells that were not incubated with a nucleic acid sequence that is complementary to an mRNA encoding ABCD1 or with a control antisense oligonucleotide or siRNA. A reference level can be obtained, for example, from untreated subjects that do not have X-ALD. "Untreated" refers to the lack of therapy from administration of a vector expressing an ABCD1 transgene.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Other definitions appear in context throughout this disclosure.

Compositions and Methods

Compositions and methods of the invention provide treatments for X-linked adrenoleukodystrophy (X-ALD). X-linked adrenoleukodystrophy is a genetic disorder, caused by mutations in the ABCD1 gene, that occurs primarily in males and mainly affects the nervous system and the adrenal glands. Myelin of the brain and spinal cord deteriorate (demyelination), which reduces the functional ability of the nerves. In addition, damage to the outer layer of the adrenal glands (adrenal cortex) causes a shortage of certain hormones (adrenocortical insufficiency). There are several distinct types of X-linked adrenoleukodystrophy, including a childhood cerebral form, an adrenomyeloneuropathy (AMN) type, and a form called Addison disease. As used herein, X-ALD does not include "neonatal adrenoleukodystrophy," which belongs to the peroxisomal biogenesis disorders of the Zellweger spectrum and is unrelated to mutations in ABCD1. Methods for diagnosing or identifying subjects with X-ALD or AMN are known in the art and can include measurement of plasma very long chain fatty acid (VLCFA) levels and/or genetic testing; see, e.g., Engelen et al., Orphanet J Rare Dis. 2012; 7: 51; Aubourg and Chaussain, Horm Res. 2003; 59 Suppl 1:104-5; Steinberg et al., Curr Protoc Hum Genet. 2008 Chapter 17:Unit 17.6; Steinberg S J, Moser A B, Raymond G V. X-Linked Adrenoleukodystrophy. 1999 Mar. 26 [Updated 2015 Apr. 9]. In: Pagon R A, Adam M P, Ardinger H H, et al., editors. GeneReviews® [Internet]. Seattle (WA): University of Washington, Seattle; 1993-2016. Available from: ncbi.nlm.nih.gov/books/NBK1315/).

Mutations in the ABCD1 gene cause X-linked adrenoleukodystrophy. The ABCD1 gene encodes the adrenoleukodystrophy protein (ALDP), which is involved in transporting very long-chain fatty acids (VLCFAs) into peroxisomes. ABCD1 gene mutations result in a deficiency of ALDP. When this protein is lacking, the transport and subsequent breakdown of VLCFAs is disrupted, causing abnormally high levels of these fats in the body. The accumulation of VLCFAs may be toxic to the adrenal cortex and myelin.

Correction of the genetic defect by gene therapy presents a viable therapy. Targeted, specific delivery of the ABCD1 gene to the CNS is essential to avoid toxicity in peripheral organs. This can be achieved, for example, by administering an adeno-associated virus (AAV) vector encoding ABCD1 via intrathecal administration.

Sequences encoding the ABCD1 cDNA and its expressed protein are well known, and can be found, for example at Genbank Accession Nos. NG_009022.2 and NP_000024.2.

"AAV" is adeno-associated virus, and may be used to refer to the recombinant virus vector itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on its serology, e.g., there are eleven serotypes of AAVs, AAV1-AAV11, and the term encompasses pseudotypes with the same properties. Many of these serotypes have unique biological properties from other AAV serotypes (e.g. cell surface receptor binding, intracellular trafficking). Thus, for example, AAVS serotypes include AAV with the biological properties of AAVS, e.g., a pseudotyped AAV comprising AAVS capsid and an AAV genome which is not derived or obtained from AAVS or which genome is chimeric.

An "AAV vector" refers to a viral particle composed of at least one AAV capsid protein and an encapsidated polynucleotide. If the particle comprises a heterologous polynucleotide (i.e., a polynucleotide other than a wild-type AAV genome such as a transgene to be delivered to a mammalian cell), it can be referred to as "rAAV (recombinant AAV)." An AAV "capsid protein" includes a capsid protein of a wild-type AAV, as well as modified forms of an AAV capsid protein which are structurally and or functionally capable of packaging an AAV genome and bind to at least one specific cellular receptor which may be different than a receptor employed by wild type AAV. A modified AAV capsid protein includes a chimeric AAV capsid protein such as one having amino acid sequences from two or more serotypes of AAV, e.g., a capsid protein formed from a portion of the capsid protein from AAVS fused or linked to a portion of the capsid protein from AAV2, and a AAV capsid protein having a tag or other detectable non-AAV capsid peptide or protein fused or linked to the AAV capsid protein, e.g., a portion of an antibody molecule which binds the transferrin receptor may be recombinantly fused to the AAV-2 capsid protein.

Cells capable of producing AAV are known in the art and include, but are not limited to 293 cells, HeLa cells and insect cells.

In certain embodiments, methods of producing high titers of AAV can be utilized to maximize administration of ABCD1. Transfected producer cells grown in culture can be incubated with a nucleic acid sequence that is complementary to an mRNA encoding ATP binding cassette subfamily D member 1 (ABCD1) and ii) transfected with an AAV vector comprising a nucleotide sequence encoding ABCD1 into the cells (e.g., AAV9-ABCD1 vector). The amount of ABCD1 mRNA expressed from the AAV vector is decreased, thereby increasing AAV-ABCD1 vector yield in cell lysate and/or media by about 1 fold to about 50 fold compared to a reference standard. In certain embodiments, the AAV-ABCD1 vector yield in cell lysate and/or media is increased by about 4 fold. Vector titers can be determined according to methods well known in the art. Typically, this is performed using dot blots or quantitative PCR to measure AAV genomes. In general, AAV vector yields can be about $1\times10^{10}$ genome copies/ml (gem') to about $1\times10^{16}$ gc/ml from cell lysates and from media.

In specific embodiments, the reference standard comprises AAV-ABCD1 vector yield in cell lysate and/or media from producer cells that were not incubated with a nucleic acid sequence that is complementary to an mRNA encoding ABCD1.

This can be achieved, for example, by providing an antisense oligonucleotide that is complementary to ABCD1 mRNA. Other nucleic acid sequences for use in practicing the methods of the invention and that are complementary to ABCD1 mRNA can be those which inhibit post-transcriptional processing of ABCD1, such as an interfering RNA, including but not limited to an shRNA or siRNA, or an antagomir.

Sequences encoding the ABCD1 mRNA are well known, and can be found, for example at Genbank Accession Nos. NM_000033.3.

Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to ABCD1 mRNA. Thus, oligonucleotides are chosen which are sufficiently complementary to the target, i.e., hybridize sufficiently well and with sufficient specificity, to give the desired effect.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target.

It is understood in the art that a complementary nucleic acid sequence need not be 100% complementary to that of its target nucleic acid to be specifically hybridizable. A complementary nucleic acid sequence of the invention is specifically hybridizable when binding of the sequence to the target DNA or RNA molecule interferes with the normal function of the target DNA or RNA to cause a loss of activity, and there is a sufficient degree of complementarity to avoid non-specific binding of the sequence to non-target sequences under conditions in which specific binding is desired, i.e., under physiological conditions in the case of in vivo assays or therapeutic treatment, and in the case of in vitro assays, under conditions in which the assays are performed under suitable conditions of stringency. For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

It is preferred that the antisense oligonucleotides of the present invention comprise at least 80% sequence complementarity to a target region within the target nucleic acid, moreover that they comprise 90% sequence complementarity and even more preferable to comprise 95% sequence complementarity to the target region within the target nucleic acid sequence to which they are targeted. For example, an antisense compound in which 18 of 20 nucleobases of the antisense oligonucleotide are complementary, and would therefore specifically hybridize, to a target region would represent 90 percent complementarity. Percent complementarity of an antisense compound with a region of a target nucleic acid can be determined routinely using basic local alignment search tools (BLAST programs) (Altschul et al., J. Mol. Biol., 1990, 215, 403-410; Zhang and Madden, Genome Res., 1997, 7, 649-656). Antisense and other compounds of the invention, which hybridize to ABCD1 mRNA, are identified through experimentation, and representative sequences of these compounds are herein below identified as preferred embodiments of the invention.

In another embodiment, the nucleic acid sequence that is complementary to ABCD1 mRNA can be an interfering RNA, including but not limited to an shRNA or siRNA. Interfering RNA includes, but is not limited to small interfering RNA ("siRNA") and small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference.

In certain embodiments of the invention, the interfering RNA coding region encodes a self-complementary RNA molecule having a sense region, an antisense region and a loop region. Such an RNA molecule when expressed desirably forms a “hairpin” structure, and is referred to herein as an “shRNA.” The loop region is generally between about 2 and about 10 nucleotides in length. In a preferred embodiment, the loop region is from about 6 to about 9 nucleotides in length. In one such embodiment of the invention, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. For details, see Brummelkamp et al., Science 296:550-553, (2002); Lee et al, Nature Biotechnol., 20, 500-505, (2002); Miyagishi and Taira, Nature Biotechnol 20:497-500, (2002); Paddison et al. Genes & Dev. 16:948-958, (2002); Paul, Nature Biotechnol, 20, 505-508, (2002); Sui, Proc. Natl. Acad. Sd. USA, 99(6), 5515-5520, (2002); Yu et al. Proc Natl Acad Sci USA 99:6047-6052, (2002).

The target RNA cleavage reaction guided by siRNAs is highly sequence specific. In general, siRNA containing a nucleotide sequences identical to a portion of the target gene (i.e., ABCD1) are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition.

In yet another embodiment, the nucleic acid sequence that is complementary to ABCD1 mRNA is an antagomir. Antagomirs are single stranded, double stranded, partially double stranded and hairpin structured chemically modified oligonucleotides that target a microRNA. Preferably, an antagomir featured in the invention includes a nucleotide sequence sufficiently complementary to hybridize to a miRNA target sequence of about 10 to 25 nucleotides, preferably about 15 to 20 nucleotides.

In certain embodiments, antagomirs are RNA-like oligonucleotides that harbor various modifications for RNase protection and pharmacologic properties such as enhanced tissue and cellular uptake. An antagomir can differ from normal RNA by having complete 2'-O-methylation of sugar, phosphorothioate backbone and a cholesterol-moiety at 3'-end. Phosphorothioate modifications provide protection against RNase activity and their lipophilicity contributes to enhanced tissue uptake. In a preferred embodiment, the antagomir includes six phosphorothioate backbone modifications; two phosphorothioates are located at the 5'-end and four at the 3'-end. Antagomirs of the present invention can also be modified with respect to their length or otherwise the number of nucleotides making up the antagomir.

The nucleic acid sequences used to practice this invention, whether RNA, cDNA, genomic DNA, vectors, viruses or hybrids thereof, can be isolated from a variety of sources, genetically engineered, amplified, and/or expressed/generated recombinantly. Recombinant nucleic acid sequences can be individually isolated or cloned and tested for a desired activity. Any recombinant expression system can be used, including e.g. in vitro, bacterial, fungal, mammalian, yeast, insect or plant cell expression systems.

Nucleic acid sequences of the invention can be inserted into delivery vectors and expressed from transcription units within the vectors (e.g., AAV vectors). The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion, ligation, transformation, plasmid purification, and DNA sequencing, for example as described in Sambrook et al. Molecular Cloning: A Laboratory Manual. (1989)), Coffin et al. (Retroviruses. (1997)) and “RNA Viruses: A Practical Approach” (Alan J. Cann, Ed., Oxford University Press, (2000)). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus. The recombinant vectors capable of expressing the nucleic acids of the invention can be delivered as described herein, and persist in target cells (e.g., stable transformants).

Nucleic acid sequences used to practice this invention can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Nucleic acid sequences of the invention can be stabilized against nucleolytic degradation such as by the incorporation of a modification, e.g., a nucleotide modification. For example, nucleic acid sequences of the invention include a phosphorothioate at least the first, second, or third internucleotide linkage at the 5' or 3' end of the nucleotide sequence. As another example, the nucleic acid sequence can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the nucleic acid sequence can include at least one 2'-O-methyl-modified nucleotide, and in some embodiments, all of the nucleotides include a 2'-O-methyl modification.

Techniques for the manipulation of nucleic acids used to practice this invention, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

ABCD1 vector administration provided by intravenous (IV) or intracerebroventricular (ICV) administration has recently been determined to cause cardiac toxicity. Intrathecal administration is a route of administration comprising injection of desired agents into the subarachnoid space of the spinal canal, thereby providing the agents into the cerebrospinal fluid (CSF). Using intrathecal administration, ABCD1 expression from a vector within in the central nervous system is less than ABCD1 expression from a vector within peripheral organs, such as the heart. Excess ABCD1 expression in peripheral organs can result in toxicity and therefore, intrathecal administration of ABCD1 vectors comprises an improved method of therapy for X-ALD, e.g., for AMN.

In some embodiments, the intrathecal administration is via a pump. The pump may be a surgically implanted osmotic pump. In certain embodiments, the osmotic pump is implanted into the subarachnoid space of the spinal canal to facilitate intrathecal administration.

In certain embodiments, human subjects receive a one-time treatment of intrathecally delivered vector (e.g., AAV9) comprising ABCD1 in an amount of about $1\times10^{13}$ GC to about $10\times10^{13}$ GC over a period of about 24 hours.

The slow continuous intrathecal infusion of the AAV9-hABCD1 can be scaled up to humans by using an osmotically driven pump such as the DUROS® implant, ALZA Corporation (Mountain View, CA). See also, J. C. Wright, J. Culwell, Long-term controlled delivery of therapeutic agents by the osmotically driven DUROS® implant, in: M. J. Rathbone, J. Hadgraft, M. S. Roberts (Eds.), Modified-Release Drug Delivery Technology, Informa Healthcare, New York, 2008, pp. 143-149.

Osmotic delivery devices and their component parts have been described, for example, in U.S. Pat. Nos. 5,609,885; 5,728,396; 5,985,305; 5,997,527; 6,113,938; 6,132,420; 6,156,331; 6,217,906; 6,261,584; 6,270,787; 6,287,295; 6,375,978; 6,395,292; 6,508,808; 6,544,252; 6,635,268; 6,682,522; 6,923,800; 6,939,556; 6,976,981; 6,997,922; 7,014,636; 7,207,982; 7,112,335; 7,163,688; U.S. Patent Publication Nos. 2005-0175701, 2007-0281024, and 2008-0091176.

The DUROS® delivery device typically consists of a cylindrical reservoir which contains the osmotic engine, piston, and drug formulation. The reservoir is capped at one end by a controlled-rate water-permeable membrane and capped at the other end by a diffusion moderator through which drug formulation is released from the drug reservoir. The piston separates the drug formulation from the osmotic engine and utilizes a seal to prevent the water in the osmotic engine compartment from entering the drug reservoir. The diffusion moderator is designed, in conjunction with the drug formulation, to prevent body fluid from entering the drug reservoir through the orifice.

The DUROS® device releases a therapeutic agent at a predetermined rate based on the principle of osmosis. Extracellular fluid enters the DUROS® device through a semi-permeable membrane directly into a salt engine that expands to drive the piston at a slow and even delivery rate. Movement of the piston forces the drug formulation to be released through the orifice or exit port at a predetermined sheer rate. In one embodiment of the present invention, the reservoir of the DUROS® device is load with a suspension formulation of the present invention, comprising, for example, $1\times10^{11}$ gc AAV9-hABCD1, wherein the device is capable of delivering the suspension formulation to a subject over an extended period of time at a pre-determined, therapeutically effective delivery rate.

Other implantable, drug delivery devices may be used in the practice of the present invention and may include regulator-type implantable pumps that provide constant flow, adjustable flow, or programmable flow of the compound, such as those available from Codman & Shurtleff, Inc. (Raynham, Mass.), Medtronic, Inc. (Minneapolis, Minn.), and Tricumed Medinzintechnik GmbH (Germany).

The present invention is additionally described by way of the following illustrative, non-limiting Examples that provide a better understanding of the present invention and of its many advantages.

EXAMPLES

The following Examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following Examples do not in any way limit the invention.

Example 1: Production of AAV9-ABCD1 in the Presence of siRNA Specific for ABCD1 mRNA Improves AAV Vector Titers from Transfected 293T Cells A high amount of cell death/cytopathic effects during production of AAV9-ABCD1 has been previously observed, likely due to overexpression of ABCD1 protein in producer cells. This toxicity reduced AAV vector yields. To mitigate the toxicity and improve vector yields, ABCD1 mRNA was targeted using a pool of siRNAs.

AAV packing was carried out as follows. 1-1.5×$10^7$ 293T cells were plated on 15 cm plates in and cultured overnight.

TABLE 1

| Packaging and Collection Media |
|---|
| DMEM High Glucose, HEPES |
| DMEM 10% FBS 1% p/s |
| DMEM 2% FBS 1% p/s |
| 2.5 mM Hepes buffer |
| 2M CaCl |
| 2 × Hebs buffer, pH 7.04-7.047 |
| PBS |
| Trypsin |
| NaCl, 50 mM HEPES, 1.5 mM |
| Na2HPO4 |
| 5 mM EDTA |

On day 2, transfection mix was prepared as follows:

TABLE 2

| Transfection Mix | |
|---|---|
| Tube A | Tube B |
| Vector Construct 10 ug | 2 × Hebs 780 ul |
| Adenovirus helper 26 ug | |
| **Serotype plasmid 12 ug | |
| 2M CaCl 96.9 | |
| 2.5 mM Hepes up to 780 ul | |
| Total Volume 780 ul | Total Volume 780 ul |

Tube A and Tube B were combined drop-wise while vortexing for 1 minute. The mix was incubated at room temperature for 20 minutes. 1.5 ml of virus mix per 15 cm plate was added, distributing drop-wise over the surface of the plate. Plates were tilted to mix evenly and incubated overnight. At day 3, media was replaced with DMEM 2% FBS 1% p/s. At day 5, half of the plate media volume was removed from each plate. Cells were collected from plates by washing with remaining media or gently using a cell scraper. Cells were spun down at 1300 RPM for 5 minutes. Supernatant was removed. Cells were loosened by flicking the bottom of the tube and re-suspended in 1 ml EDTA PBS per plate of cells and spun at 1300 RPM for 5 minutes. Cells were re-suspended in 1 ml lysis buffer per plate and optionally stored at −80 C. Following gradient purification, virus was buffer exchanged into PBS, quantified by qPCR, and used for experimentation.

On the day of 293T cell plating, cells were transfected with the pool of siRNA specific for ABCD1 mRNA or a non-targeting control siRNA. Another control was an AAV9 vector encoding GFP (AAV9-GFP) in the presence of the ABCD1 siRNA. The following day both samples were transfected with AAV plasmids to produce AAV9-ABCD1.

The siRNA protocol has multiple steps:

1. Prepare 5 μM of pooled (25% of each of 4 siRNAs) siRNA solution in 1×siRNA buffer (GE Healthcare) or another appropriate RNase-free solution from stock solution.
2. In separate tubes, dilute the siRNA (100 ul in tube1) and the appropriate DharmaFECT transfection reagent (30 ul in tube2) with serum-free DMEM medium to 2 ml volume respectively.
3. Gently mix the contents of each tube by pipetting carefully up and down. Incubate for 5 minutes at room temperature.
4. Add the contents of Tube 1 to Tube 2, for a total volume of 4 ml. Mix by pipetting carefully up and down and incubate for 20 minutes at room temperature. Add 12 ml of complete DMEM (10% FBS) to the 4 ml.
5. Add 4 ml of resuspended 293T cells in complete media that are at a concentration of 3.75e6 cells/ml (total 1.5E7 cells) to the 16 ml of the transfection mixture from step 4 (final siRNA concentration of 25 nM).
6. Plate into 15 cm dish and incubate 24 h.
7. Change media to complete DMEM 10% FBS 1 h before calcium phosphate transfection with AAV plasmids.
8. Proceed with standard AAV production and purification protocol.

Three days post transfection cells were harvested, lysed, and vector yields (in genome copies) was determined by qPCR as follows:

TABLE 3

| qPCR Materials |
|---|
| F2: CCTCGACTGTGCCTTCTAG (SEQ ID NO. 1) |
| R2: TGCGATGCAATTTCCTCAT (SEQ ID NO. 2) |
| Probe: 5'FAM-tgccagccatctgttgtttgcc-MGB (SEQ ID NO. 3) |
| Nuclease free water |
| F and R qPCR primers |
| TM FAM Probe |
| TaqMan Fast universal PCR Master Mix |
| PCR plates for 7500 (Fast) Qpcr |
| PCR plate film |

The qPCR protocol has multiple steps:

1. Dilute vector 1:100-1:1000 in nuclease-free water and vortex. Use in qPCR.
2. Use plasmid 675.5 (5999 bp) as genome copy (GC) standard. Create a standard from $10^7$-$10^2$ gc/mL.
3. Prepare the master mix in an amount large enough to measure the standards and samples in triplicate. The master mix includes 2 ul H2O, 1.2 ul primer mix (F and R=5 ul of each 100 um stock in 90 ul of water), 1 ul primer mix (F and R=6 ul of each 100 um stock in 88 ul of water), 0.8 ul TM FAM Probe 2.5 uM, 1 ul TM FAM Probe 2 uM (4 ul of 100 uM stock+196 ul water), and 5 ul of TaqMan Fast universal PCR Master Mix 2×.
4. Mix and aliquot 9 ul in wells of plate.
5. Add 1 ul of template diluted in water.
6. Program 7500 machine to have thermal cycling parameters where stage 1 has reps 1, 95° C.:20 and stage 2 has reps 40, 95° C.:03; 60° C.:30.
7. Analyze data. Slope for standard should be ~−3.3.

The yield is reported as relative titer in which the AAV9-GFP sample was set arbitrarily at 100% and the other two samples normalized to this value. Production of AAV9-ABCD1 in the presence of the siRNA pool against ABCD1 mRNA improved the vector titer (and yield) by approximately 4-fold compared to the control siRNA (FIG. 1).

TABLE 4

| siRNAs Targeting ABCD1 | |
|---|---|
| SEQ ID NO. 4 | CGGAUCAUGUCGUCGUACA |
| SEQ ID NO. 5 | CGGAGGAGAUCGCCUUCUA |
| SEQ ID NO. 6 | GUUCAGCGCUGUCACUUCA |
| SEQ ID NO. 7 | GAACGCCUGUGGUAUGUUA |

Figure 2:
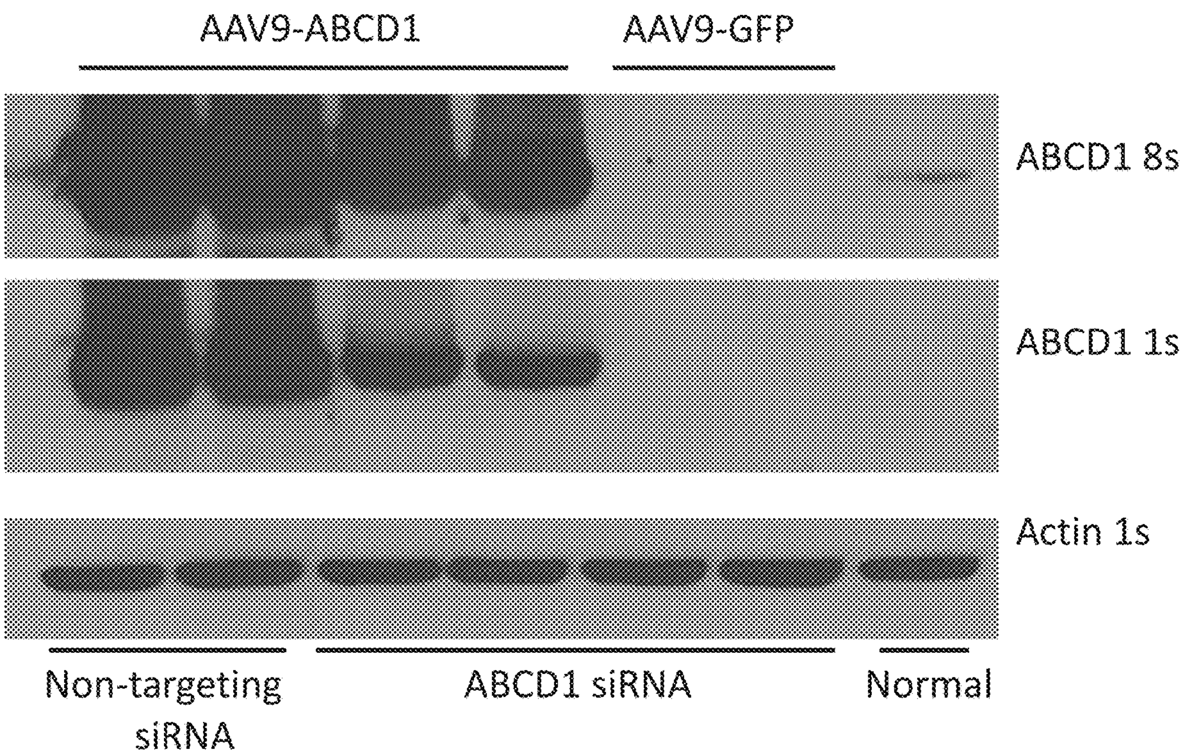
FIG. 2 depicts reduced ABCD1 protein in AAV-ABCD1 transfected cells incubated with an siRNA pool specific for ABCD1 mRNA.

293T cells were transfected with control siRNA (FIG. 2, lanes 1, 2), siRNA pool against ABCD1 mRNA (FIG. 2, lanes 3-6) or untransfected (FIG. 2, lane 7, "normal" refers to endogenous levels of ABCD1 protein in 293T cells). AAV-ABCD1 plasmid (FIG. 2, lanes 1-4) or AAV-GFP plasmid (FIG. 2, lane 5, 6) was transfected the following day. Three days later, cell lysates were electrophoresed on an SDS PAGE gel and an immunoblot for ABCD1 protein was performed to assess siRNA knockdown. Actin blotting was performed for loading control. 8 s and 1 s refers to 8 second and 1 second exposure of the radiographic film, respectively. The ABCD1 siRNA reduces the level of overexpressed ABCD1 compared to control siRNA.

Figure 3:
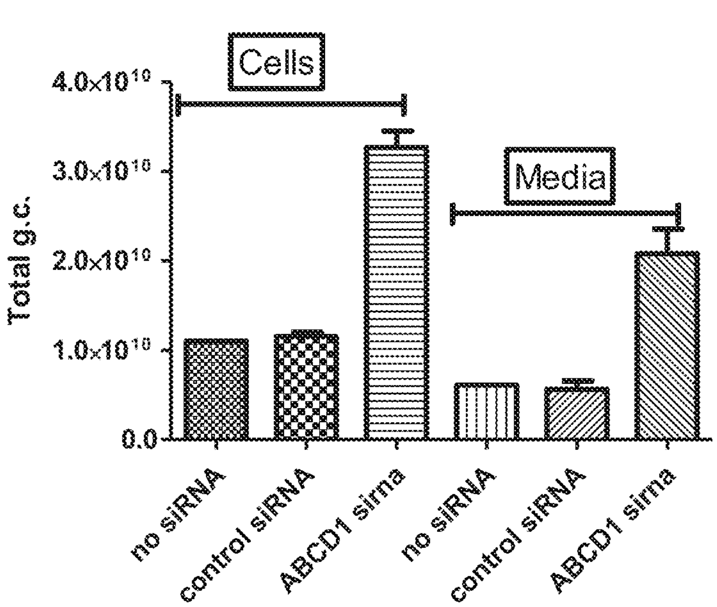
FIG. 3 depicts improved AAV9-ABCD1 vector titers from transfected 293T cells incubated with siRNA specific for ABCD1 mRNA in both cell lysates and conditioned media.

293T cells were left untransfected (no siRNA) or transfected with control siRNA or the siRNA pool against ABCD1 mRNA. The following day cells were transfected with AAV plasmids to produce AAV9-ABCD1. On day 3 post transfection of AAV plasmids, qPCR was performed to determine the amount of vector (g.c.) in cell lysate and in the media of the transfected cells. An approximate 3-4 fold increase in AAV9-ABCD1vector yield in both cell lysate and media was observed (FIG. 3).

Example 2: Intrathecal Delivery of rAAV9-ABCD1 by Osmotic Pump in a Mouse Model of Adrenomyeloneuropathy Leads to More Uniform and Widespread Gene Delivery to the CNS Self-complementary AAV9 GFP(scAAV9GFP) and rAAV9 encoding ABCD1 (rAAV9-ABCD1) were delivered to Abcd1−/− mice intrathecally (IT) either by bolus over a 2 minute duration or by osmotic pump over 24 hour duration with PBS injection as sham control. Two weeks after injection, mice were sacrificed and perfused with 4% PFA. Tissues were then collected, sectioned and stained for immunofluorescence analysis.

scAAV9-GFP delivered IT by osmotic pump led to widespread expression across CNS-relevant cell types and DRGs in a dose-dependent manner. Spinal cord and DRG had higher expression compared with brain, but GFP expression was also detected in peripheral organs (liver, heart and adrenal gland), with highest expression seen at $3\times10^{11}$ GC.

Figure 4:
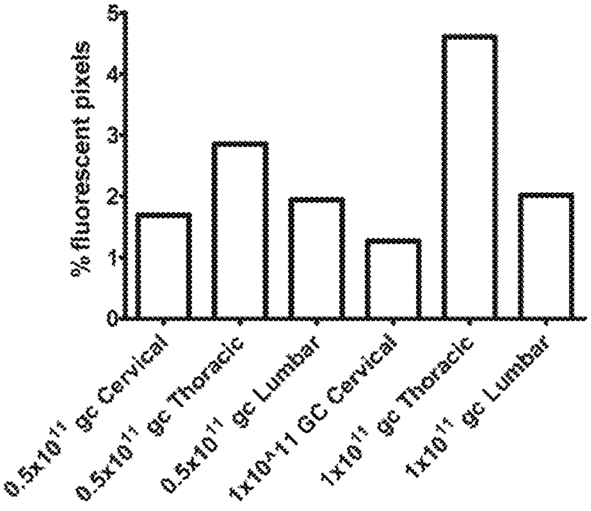
FIG. 4 depicts distribution of rAAV9-ABCD1 following intrathecal bolus delivery over 2 minutes.

A similar distribution pattern of ABCD1 protein was detected after rAAV9-ABCD1 intrathecal pump delivery. In general, higher doses ($2\times10^{11}$ GC and $1\times10^{11}$ GC) led to more expression in CNS and peripheral organs compared with a lower dose ($0.5\times10^{11}$ GC). By comparison, intrathecal bolus delivery over 2 minutes led to the highest amount of ABCD1 expression in the thoracic region, however, even a higher dose ($1\times10^{11}$ gc) did not lead to more widespread delivery in cervical and lumbar regions (FIG. 4).

Figure 5:
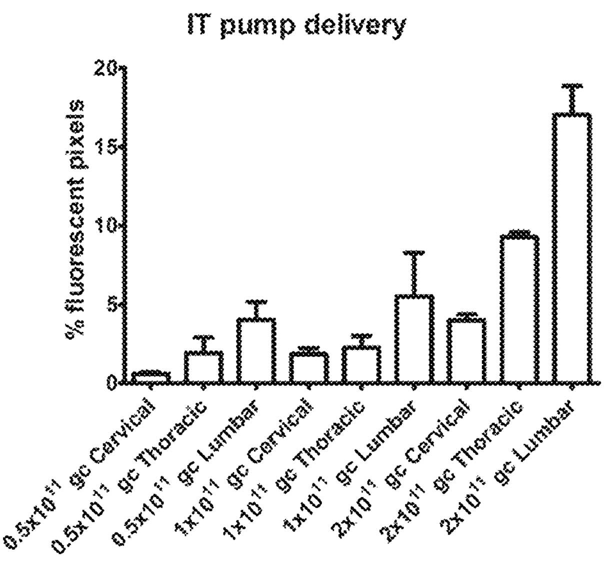
FIG. 5 depicts distribution of rAAV9-ABCD1 following intrathecal pump infusion of rAAV9-ABCD1 over 24 hours.
Figure 6:
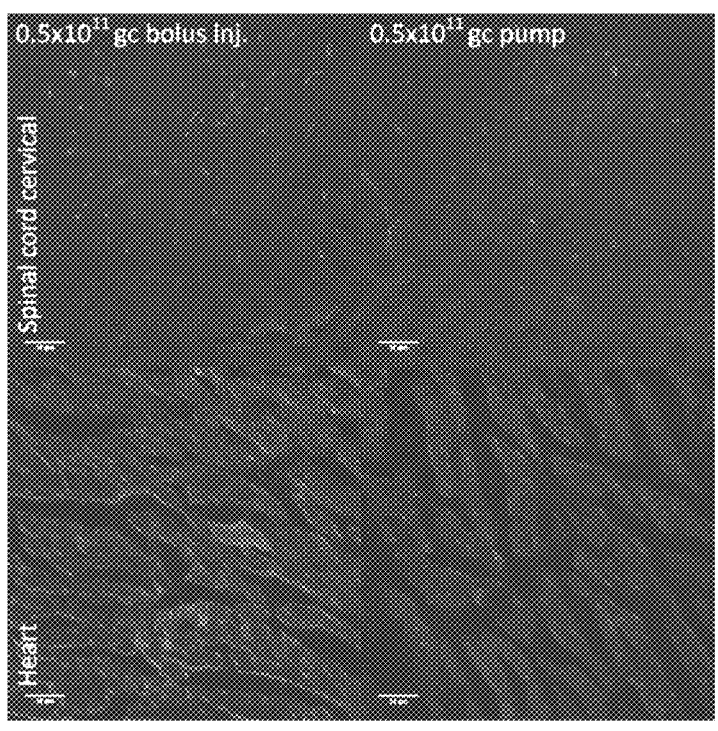
FIG. 6 depicts low dose ($0.5\times10^{11}$ gc) bolus and pump delivery of AAV9-ABCD1.
Figure 7:
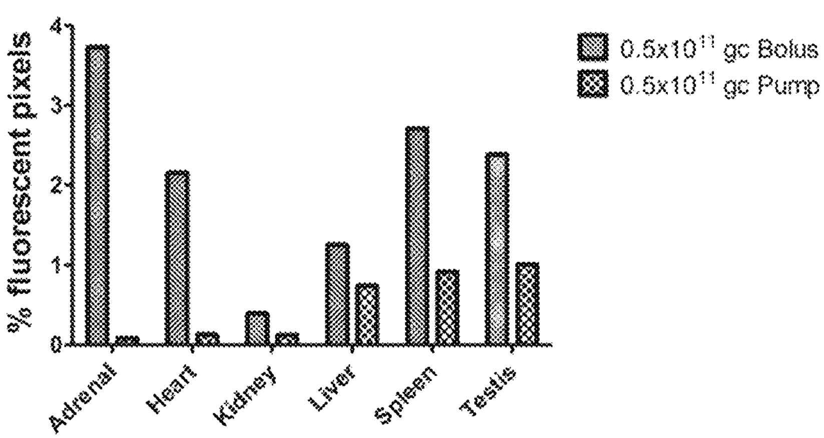
FIG. 7 depicts higher expression of ABCD1 across peripheral organs (outside the CNS) two weeks after bolus injection of AAV9-ABCD1 compared to pump infusion of AAV9-ABCD1.
Figure 8:
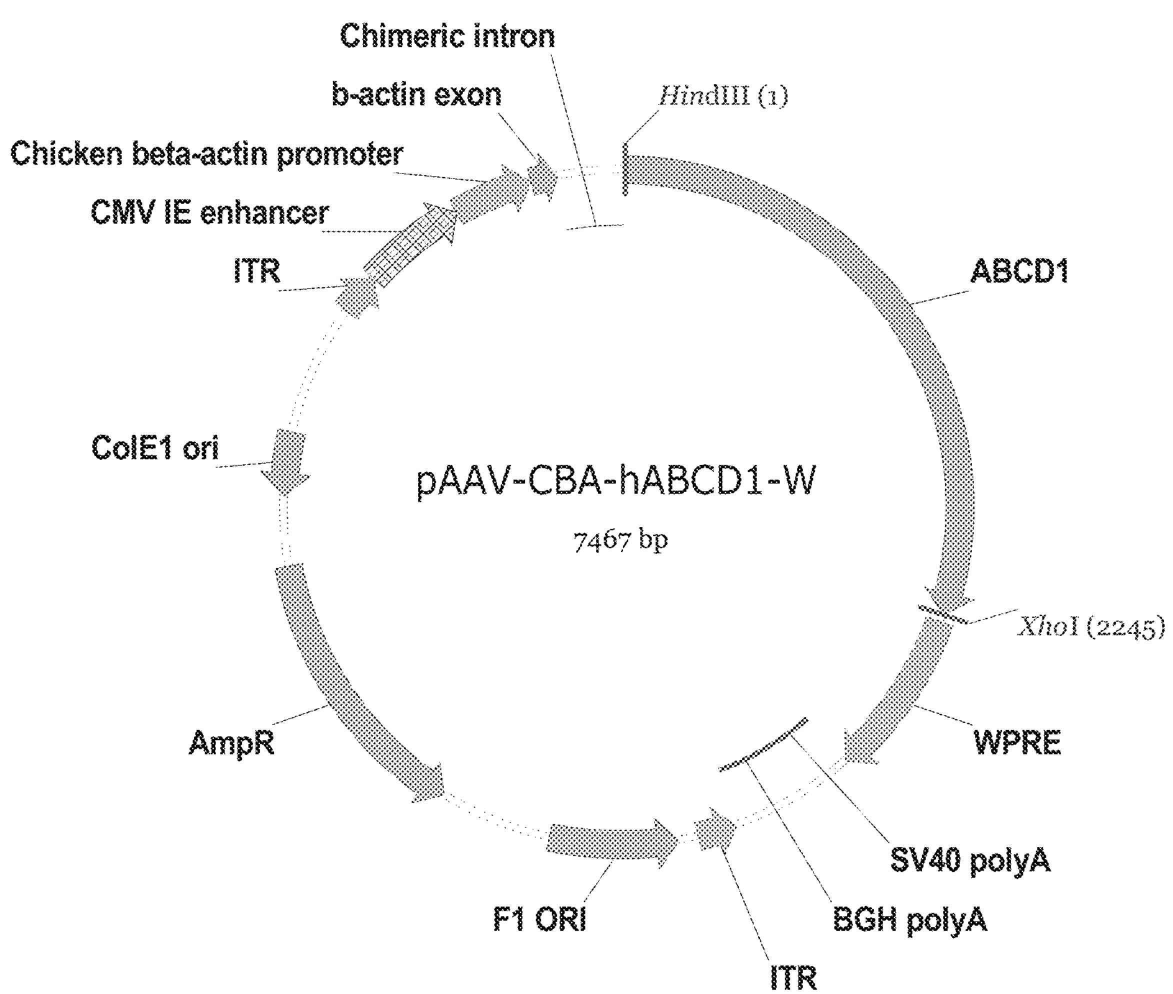
FIG. 8 depicts a vector map of AAV9-ABCD1.
Figure 9:
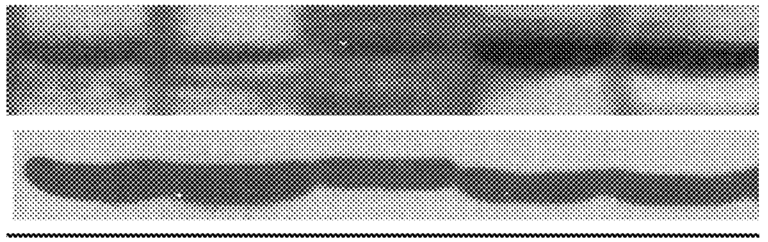
FIG. 9 depicts distribution of endogenous ABCD1 across different organs.
Figure 10:
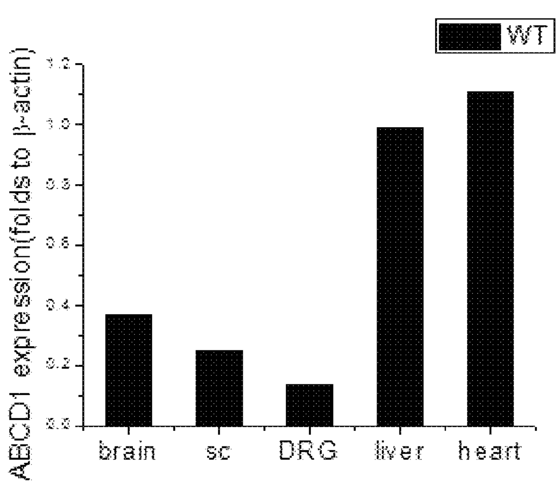
FIG. 10 depicts distribution of endogenous ABCD1 across different organs.
Figure 11:
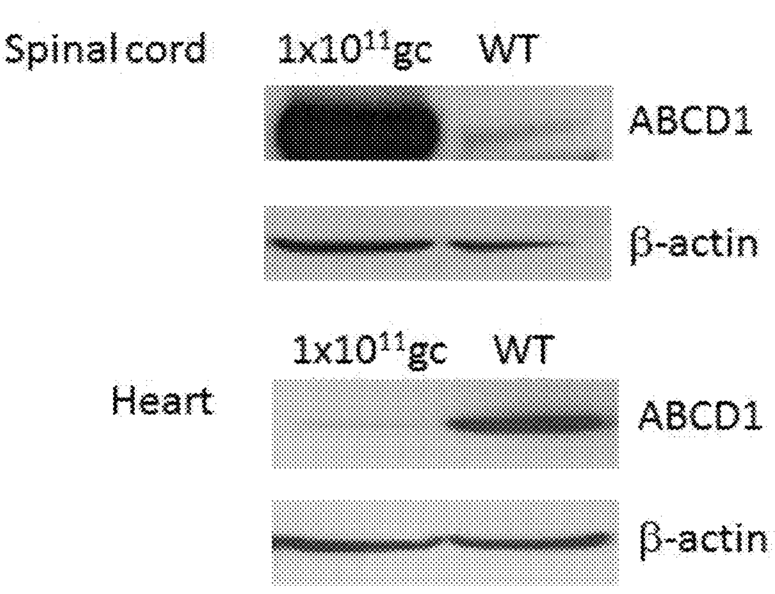
FIG. 11 depicts expression of ABCD1 after IT pump in Abcd1−/− mouse.
Figure 12:
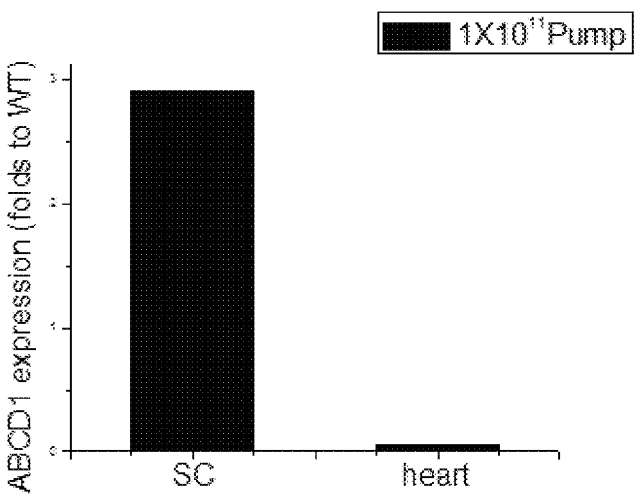
FIG. 12 depicts expression of ABCD1 after IT pump in Abcd1−/− mouse.

Notably, widespread expression of ABCD1 across CNS was even detected after low dose, direct intrathecal bolus injection of $0.5\times10^{11}$ GC (FIG. 5). For example, $0.5\times10^{11}$ GC bolus and pump delivery show similar expression of ABCD1 in the cervical cord, while heart tissue demonstrated higher expression after bolus injection (FIG. 6). It was concluded that the same dose delivered by pump led to higher expression in brain and spinal cord far from the injection site and comparatively less leakage to peripheral organs compared with bolus injection (FIG. 7). Delivering rAAV9-ABCD1 at $0.5\times10^{11}$ GC by intracerebroventricular administration results in behavioral improvement in the Abcd1−/− mouse despite localized expression in brain. Therefore, even better performance at this dose using the outlined intrathecal pump delivery can be achieved. At a dose of $1\times10^{11}$ GC administered via intrathecal pump, ABCD1 expression in the central nervous system was about 3 fold higher than expression of ABCD1 in the central nervous system of an untreated subject that does not have X-ALD (e.g., wild-type). Importantly, ABCD1 expression in peripheral organs was about 90% less than expression of ABCD1 expression in peripheral organs of an untreated subject that does not have X-ALD (see FIG. 11, where protein expression among different tissue types in Western blots was normalized to endogenous wild-type levels).

In conclusion, rAAV9-mediated ABCD1 gene transfer via intrathecal osmotic pump leads to more uniform and widespread gene delivery to the CNS with reduced leakage into the systemic circulation compared with intrathecal bolus injection.

Figure 13:
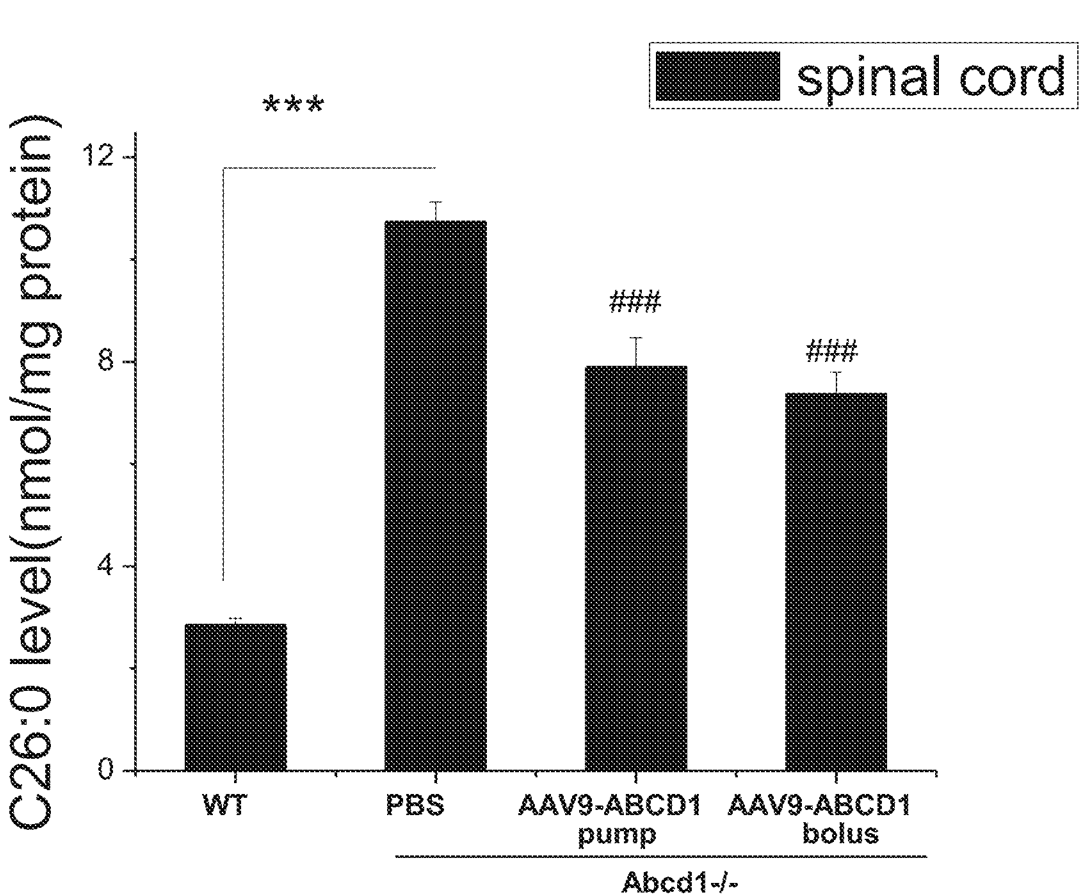
FIG. 13 depicts spinal cord C26:0 level 15 days after IT pump and PT bolus injection.

Example 3: rAAV9-Mediated ABCD1 Gene Transfer Via Intrathecal Osmotic Pump Leads to a Reduction in C26: 0 Levels in the Spinal Cord C26:0 is the biochemical hallmark of adrenomyeloneuropathy. To assess for the presence of free very long chain fatty acids (VLCFA) after AAV9 gene delivery, lipidomic analysis was performed on spinal cord samples. Absolute values of C26:0 and C24:0 as well as ratios of C26:0/C22:0 are reported. It was determined that rAAV9-mediated ABCD1 gene transfer via intrathecal osmotic pump ($1\times10^{11}$ gc) leads to a 20% reduction in C26:0 levels in the spinal cord (FIG. 13). The levels after intrathecal osmotic pump delivery are comparable to those after intrathecal bolus delivery but avoid systemic leakage.

Figure 14:
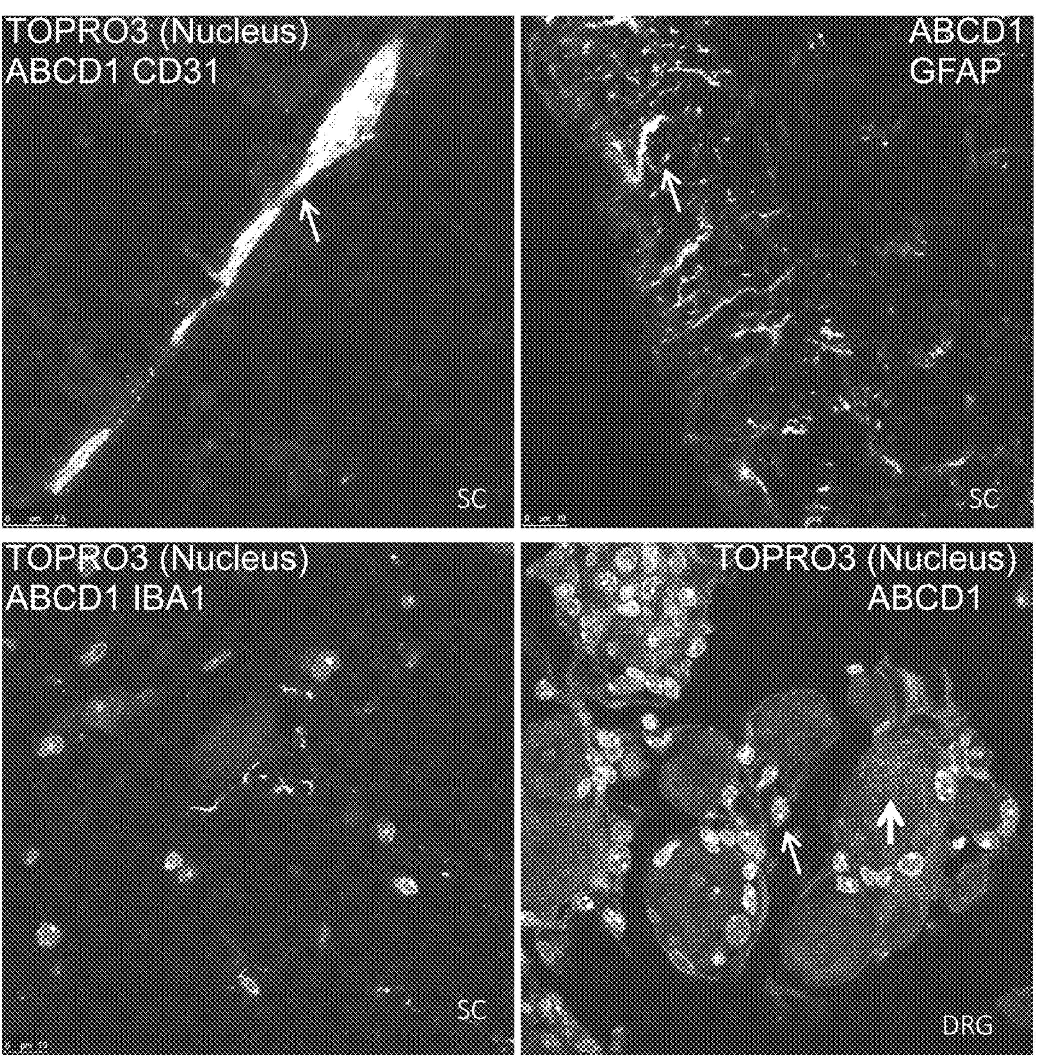
FIG. 14 depicts ABCD1 expression in different cell types after IT pump delivery of AAV9-hABCD1. SC: spinal cord; DRG: dorsal root ganglion; CD31: endothelial marker; GFAP: astrocyte marker; IBA1: microglial marker; TOPRO3: nuclear counterstain; DRG shows expression speckled pattern in neuron and more prominently around neurons (satellite cells).

Immunofluorescence staining and confocal microscopy imaging were additionally conducted. For tissue section imaging, sections of spinal cord (16 μm) were cut at −25° C. using cryostat (Leica) and stored at −80° C. Sections were stained with mouse antihuman ABCD1 antibody and then contained with rabbit anti-GFAP (Dako, Carpinteria, CA), rabbit anti-IBA1 (Wako, Richmond, VA) and rabbit anti-CD31 (Abcam) respectively to localize the cell type. TOPRO-3 (Thermo Fisher Scientific) was used as fluorescent dye for nuclear counterstaining. The slides were imaged by confocal laser microscope and transduced cells counted. Estimates of ABCD1 transduced cells of each cell type were documented in 20× and 40× (for microglia) magnification images. rAAV9-mediated ABCD1 gene transfer via intrathecal osmotic pump ($1\times10^{11}$ gc) targets mainly astrocytes, endothelial cells and a few neurons in the spinal cord (FIG. 14). Within with dorsal root ganglia it targets both satellite cells and neurons (FIG. 14).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

---

What is claimed is:

1. A method of increasing titers of an adeno-associated virus 9 (AAV9) vector comprising a nucleotide sequence encoding ATP binding cassette subfamily D member 1 (ABCD1) in transfected producer cells grown in culture, said method comprising the steps of:

i) incubating a pooled combination of siRNAs consisting of SEQ ID NO: 4, SEQ ID NO: 5, SEQ ID NO: 6, and SEQ ID NO: 7, wherein each siRNA of the pooled combination of siRNAs is complementary to an mRNA encoding ABCD1 with the cells, and ii) transfecting the AAV9 vector comprising the nucleotide sequence encoding ABCD1 into the cells, wherein the producer cells are selected from the group consisting of 293 cells, HeLa cells, and insect cells.

2. The method of claim 1, wherein the producer cells are 293 cells.

3. The method of claim 1, wherein each of the siRNAs of the pooled combination of siRNAs are at an equal concentration.

4. The method of claim 3, wherein the pooled combination of siRNAs has a total concentration of 5 μM.

5. The method of claim 4, wherein the producer cells are 293 cells.

6. The method of claim 1, wherein the producer cells are HeLa cells.

7. The method of claim 1, wherein the producer cells are insect cells.

8. A method of increasing titers of an adeno-associated virus 9 (AAV9) vector comprising a nucleotide sequence encoding ATP binding cassette subfamily D member 1 (ABCD1) in transfected producer cells grown in culture, said method comprising the steps of:

i) incubating a pooled combination of siRNAs consisting of SEQ ID NO: 4, SEQ ID NO: 5, SEQ ID NO: 6, and SEQ ID NO: 7, wherein each siRNA of the pooled combination of siRNAs is complementary to an mRNA encoding ABCD1 with the cells, wherein each of the siRNAs of the pooled combination of siRNAs are at an equal concentration, and wherein the pooled combination of siRNAs has a total concentration of 5 μM, and ii) transfecting the AAV9 vector comprising the nucleotide sequence encoding ABCD1 into the cells, wherein the amount of ABCD1 mRNA expressed from the AAV9 vector is decreased compared to an amount prior to the transfecting, thereby increasing AAV9-ABCD1 vector yield in cell lysate and/or media by up to 4 fold compared to yield in cell lysate and/or media from producer cells that were (1) transfected with the AAV9 vector comprising the nucleotide sequence encoding ABCD1 and (2) not incubated with the pooled combination of siRNAs consisting of SEQ ID NO: 4, SEQ ID NO: 5, SEQ ID NO: 6, and SEQ ID NO: 7, wherein the producer cells are selected from the group consisting of 293 cells, HeLa cells, and insect cells.

9. The method of claim 8, wherein the producer cells are 293 cells.

10. The method of claim 8, wherein the producer cells are HeLa cells.

11. The method of claim 8, wherein the producer cells are insect cells.

* * * * *

SEQUENCE LISTING

```
Sequence total quantity: 10
SEQ ID NO: 1            moltype = DNA  length = 19
FEATURE                 Location/Qualifiers
misc_feature            1..19
                        note = synthetically generated primer
source                  1..19
                        mol_type = other DNA
                        organism = synthetic construct
SEQUENCE: 1
cctcgactgt gccttctag                                               19

SEQ ID NO: 2            moltype = DNA  length = 19
FEATURE                 Location/Qualifiers
misc_feature            1..19
                        note = synthetically generated primer
source                  1..19
                        mol_type = other DNA
                        organism = synthetic construct
SEQUENCE: 2
tgcgatgcaa tttcctcat                                               19

SEQ ID NO: 3            moltype = DNA  length = 22
FEATURE                 Location/Qualifiers
misc_feature            1..22
                        note = synthetically generated primer
source                  1..22
                        mol_type = other DNA
                        organism = synthetic construct
SEQUENCE: 3
tgccagccat ctgttgtttg cc                                           22

SEQ ID NO: 4            moltype = RNA  length = 19
FEATURE                 Location/Qualifiers
misc_feature            1..19
                        note = siRNA targeting ABCD1
source                  1..19
                        mol_type = other RNA
                        organism = synthetic construct
SEQUENCE: 4
cggatcatgt cgtcgtaca                                               19

SEQ ID NO: 5            moltype = RNA  length = 19
FEATURE                 Location/Qualifiers
misc_feature            1..19
                        note = siRNA targeting ABCD1
source                  1..19
                        mol_type = other RNA
                        organism = synthetic construct
SEQUENCE: 5
cggaggagat cgccttcta                                               19

SEQ ID NO: 6            moltype = RNA  length = 19
FEATURE                 Location/Qualifiers
misc_feature            1..19
                        note = siRNA targeting ABCD1
source                  1..19
                        mol_type = other RNA
                        organism = synthetic construct
SEQUENCE: 6
gttcagcgct gtcacttca                                               19

SEQ ID NO: 7            moltype = RNA  length = 19
FEATURE                 Location/Qualifiers
misc_feature            1..19
                        note = siRNA targeting ABCD1
source                  1..19
                        mol_type = other RNA
                        organism = synthetic construct
SEQUENCE: 7
gaacgcctgt ggtatgtta                                               19
```

-continued

```
SEQ ID NO: 8            moltype = DNA  length = 26895
FEATURE                 Location/Qualifiers
misc_feature            1..26895
                        note = Genbank Accession No. NG_009022.2
source                  1..26895
                        mol_type = genomic DNA
                        organism = Homo sapiens
SEQUENCE: 8
ccacctggcc tggccttatc ccagagcctg cttgcccttg gaccagttta tctttcaagc  60
acctgctagt gtacacctca atgtcagagt ttacagaact acagagctgg aacgacctgg  120
gaaaacctca agtctagccc agatgcagag aggtctagga tctctcccca agatatgctg  180
ccacacatct ctgtgttctc ctcctactac tacagggaat ggcaggactt cactgtgtgc  240
ttggttgctc agtcccccat tagaggccct gctccaggca attctgctgt ttaagtgact  300
ggtgagcagc actactcaga ccaaggtcac aggccagtta gcttctcttg gcttcagttc  360
tagagtgacc tgaggagcag cctcagaaac cttaggcgtc cctccttcca aggtcttgaa  420
aaaaagcaat gtaaggtggc cgtcataagc tgcatacaaa ctgcttggta taagcccacg  480
cccactgcta gaggggcctc tttttttttt ttttgagatg gagtctccct cttgttgccc  540
aggctggagt gcaatggtgc gatttaggct cactgcaacc tctgcctcgt gggttcaagc  600
aattctcctg cctcagtctc ccaagtagct gggattacag gtgcccgcca ccacgcccag  660
ctaattttgt atttttcgta gagatggggt ttcaccacgt tggccaggct gatctcgaac  720
tcctcatctc aggtgatcca ccgacctcag cctcccaaag tgctgggatt acaggcatga  780
gccaccatgt acggcctaga ggggcctcaa agtgaagaac cgactagcgg tcagcagcat  840
gggcaaaggg agcctcttcc ctccctcaag agaaagacac agcatttcat tggtctgtct  900
cctagcagcc aaaactggat gctacacatc aaaagtggca aagggttttg cagcagagac  960
cagggtctag gtcaggtagc tgccctcagc catagctcac tcaccgatga ccaacagcac  1020
aaggatgaca atgagaacca caaagaaggt gttgccatag gacactaaca actccaccag  1080
ccgggacttg aaaatcttct gccatctgtg aagaagacaa aaaggacagg agttgaagag  1140
aaagcacaca cacgagctct agggccctga gcaaaatgga aatccagctt tgtactcttc  1200
tccaatggcc gaatagccca tgcaaagtca gcctcagtgg cttgcaattc tctaatttga  1260
catccattca agactattgg aaaaaaggcc aggtgcaatg gctcacacct gtaatctcag  1320
cactttggga gaccaaggtg ggtggatcac ttgaggtcag gagtgcaaga ccaaactggc  1380
caacatggcg aaaccctgtc tctactaaaa gtacgaaaat tagccaggcg tggtggtggg  1440
cacctgtaat cccagctact caggagggtg aggcaggaga atcacttgaa cctgggaggc  1500
ggaagttgca gtgagccgag atcgcgccac tgcactccag cctgggtgac agagcgagac  1560
cttgtctcaa aaaaaaaaaa aaaaaaagat gctggtccac gtatagatca aaatgtctgg  1620
aaaactaatc tttttttttt tttttgaga cagagtcttg ctctgttgcc caggctggag  1680
tgcagaggtg taagccaccg cgcccagcct ggaaaactaa tcttaaacgt gggcagttgg  1740
ctgggcgcac tggctcacgt ctgtaaaccc agcactttgg gaggctgaga tgggcagatc  1800
acctgaggtc agaagttcaa gaccggcctg gccaacatgg tgaactccca tctctactaa  1860
aaatatatat ataaaaaaaa attagctggg catgttggca ggcacctgta gtcccagcta  1920
ctcgtgaggc tgaggcagga gaattgcttg aacccgggag gtggaggctg ctgtcagccg  1980
agcaccacac cactgcactc cagcctgggt gacagagcaa gactctgtct caaaataaaa  2040
acaaaaacaa acaaaaaaac cacaacaaca aaaagaaaac atactggtag tctctgaaaa  2100
gggaaactta cttttcattg tactcccctt tgtaatattc aaatgtttgc cccatacacg  2160
ttatttcttt aaactgtctt tccacatgat aaaccttggt ttgtctatat cccccgaccc  2220
tgttatgatg agatggaccc cagacctcac atcatttcca tccacaaatg ctttgggatg  2280
cagctctaag aagagacttc agaagtgttt acatattgtt caaatcaaca agaagccctc  2340
atcatcaggg ctagagttga atatgccaat cactgaaggc aatgatattt gtttgaatcc  2400
ggacccaaca aggtaccgat ttggcattcg gtagataaac gtcttaaatc cagcttattc  2460
tggaagctcc cccttccctc tccctctttc atttgctttt ccagtttcct ttgtgtagaa  2520
atcagattgt ctgtcctcta aagcttccca gattaaagct ccccggggcc ctctatctct  2580
gcacgtcttg tcaactgtac gaaggtgtgg ttttctacaa gaatcctcct cagacagcac  2640
tgcatacttt ctatggtatc acatcaaaga taatttttca cgaaaaaacg gcttttaaaa  2700
atacctgtgg agatttggcc ttatttgtaa tatcgtaatt taaataggga tgtgttcagg  2760
tattatacat aattaaaatt aatctccaat tcacttttaa caggtcctct gttcattaaa  2820
agggaatatg gcttcatcct ccacaggctg agtaatgttc atgcagccac tgcgcaatac  2880
cagtgagact agttaggagg acaagagtca ccaaatcagc aacaacgtga cccagtggtg  2940
caagtcttcc gaatcccacg ctaccatccc agcaccccgt ggaccaagag tgggtgggag  3000
ggcatcattt ccagaactgt aacatagatc ttcctgcctc tcgggggcat tctgaagacc  3060
agaaggcagg ggacacagga aaaggaactg agcaagtcat gacgaagcag aaccctggga  3120
agggttggca ataacaaaca caacccctgc cacccccacc ccagacaggt tctacctgtt  3180
ccatcgggtc ccaattccag ggtccaccag ctgcacacac cagtcccagg gctagggcac  3240
aggcaccctc ctgcctaact cgcctgcttg ctccataggc catacctttt aggagaaatg  3300
aagggaatgc agagaagcaa cacaacaaag acctccgcat agaggaaggt ggcaactgca  3360
gtccactgca gactcatcct gttgctagaa ggtttcccac aggaagatgt gagcttgttt  3420
cctggcaggg cacaaaaggt acgggacttg taagcgctgg gcagccaaga acatccagtt  3480
cagttaccct gcgaggctgg ggccgccact ctccaccctg accccctgca ctttgcttca  3540
aagtctctga tgcgctggcg gaagcagggc tccactcggc agggcctctt ggccagcagc  3600
gttcacaggc cccacaaact tccgttcgct ggtcaattac ctgccccctc cagcacgtgt  3660
gtcaacacgt ccagagcggc ctctcccgac gatccctgcc ccaggaagcc cgagatttcc  3720
gacgcccgtt taactgaaag gcgttcttcg ggaagagcag tgccagggca ccaagaggag  3780
gacgcctcgg cacccatcgg gcgctccctt ccccgccagg cagaactcag ccgcagaggc  3840
gggcgctctg cgggcccaaa tccccgctac caggcaggcc caaggccgca cctagtccaa  3900
gcgctgccga cgcccccgcc tcccaccgtc cccacggcgc ccgcggagag aaaccggcac  3960
ctccctcgag gatccagcgg ccttccgccc ggggccgctt cgcctccggt gggctggagg  4020
cccgcaagag cgactcctag agggcaggat tcgggaccaa gcgcaaaggc aggtctcgac  4080
caagcacctc aaggccccat acggagaaag ttctagacgc agtatcctca gaagccaggg  4140
gtccttacag tagccctcgc gggccccagc gcccacccag agcgaggggc ctccgacttg  4200
gccccggcct ggcacaccgt cccggaggcc catcccggcc gctcctccag gtggggcttc  4260
```

-continued

```
accgcccccc gccccgcccc cgagaccagc ttctagaggc gccgcccggt ttcccctcgc  4320
ccctgcctct cacacgcagg taggctgcgg gccccgagat tccccggccc ccgggcctcc  4380
ccgcgccgct cgcctctctc cctcgtcgat gggccgggga gcctccgcgg tcccggagcc  4440
cagcccggcg cgcggagccc gctcaccgag tttcccacag tcaacgtgca ggccccgccg  4500
cagcaacaga actctcccac agcagccccg gccccgcccc tcataccgcg gccggaaacc  4560
ggaagcgccc gccgggcacc gcccaccagc cctcgcgagg ccccggaggc tccgcccacc  4620
tccgcttccc accccgcccc ggagcggagg gccggcgctc cgagcgggag aggaagaggc  4680
gcctcgggct ccgggcgagc agggcggggt ggagcgagca cgcgggcggg gcggggcggg  4740
gctttgtcgg gccggcgagg gccgcttctc tagtccgcgc ggccgtccca cgtctctgtg  4800
gtgcgggagg ggccccgccg aggggcgaga acgggaggtg ggggtgtggg cgggccccgc  4860
cgagggggcga gaacagggtg gggctcccgc gcccggactc cgcccctcgc ccctcctccg  4920
cctcctcccc ttcccccgac tcgcccctgg ggaagagtgg gtggggattc tgggccggtg  4980
gaggagtcac tgtcgcttca gccaggctgc ggagcggacg gacgcgcctg gtgccccggg  5040
gaggggcgcc accgggggag gaggaggagg agaaggtgga gaggaagaga cgccccctct  5100
gcccgagacc tctcaaggcc ctgacctcag gggccagggc actgacagga caggagagcc  5160
aagttcctcc acttgggctg cccgaagagg ccgcgaccct ggagggccct gagcccaccg  5220
caccaggggc cccagcacca ccccgggggc ctaaagcgac agtctcaggg gccatcgcaa  5280
ggtttccagt tgcctagaca acaggcccag ggtcagagca acaatccttc cagccacctg  5340
cctcaactgc tgccccaggc accagcccca gtccctacgc ggcagccagc ccaggtgaca  5400
tgccggtgct ctccaggccc cggccctggc gggggaacac gctgaagcgc acggccgtgc  5460
tcctggccct cgcggcctat ggagcccaca aagtctaccc cttggtgcgc cagtgcctgg  5520
ccccggccag gggtcttcag gcgcccgccg gggagcccac gcaggaggcc tccggggtcg  5580
cggcggccaa agctggcatg aaccgggtat tcctgcagcg gctcctgtgg ctcctgcggc  5640
tgctgttccc ccgggtcctg tgccgggaga cggggctgct ggccctgcac tcggccgcct  5700
tggtgagccg caccttcctg tcggtgtatg tggcccgcct ggacggaagg ctggcccgct  5760
gcatcgtccg caaggacccg cgggcttttg gctggcagct gctgcagtgg ctcctcatcg  5820
ccctccctgc taccttcgtc aacagtgcca tccgttacct ggagggccaa ctggccctgt  5880
cgttccgcag ccgtctggtg gcccacgcct accgcctcta cttctcccag cagacctact  5940
accgggtcag caacatggac gggcggcttc gcaaccctga ccagtctctg acggaggacg  6000
tggtggcctt tgcggcctct gtggcccacc tctactccaa cctgaccaag ccactcctgg  6060
acgtggctgt gacttcctac accctgcttc gggcggcccg ctcccgtgga gccggcacag  6120
cctggccctc ggccatcgcc ggcctcgtgg tgttcctcac ggccaacgtg ctgcgggcct  6180
tctcgcccaa gttcggggag ctggtggcag aggaggcgcg gcggaagggg gagctgcgct  6240
acatgcactc gcgtgtggtg gccaactcgg aggagatcgc cttctatggg ggccatgagg  6300
tggggcaggt tggggtgccg ggcacggagg gaagcgtgtg gcagggaggc ccgggggcag  6360
gcagccgtga gcggtgggga cagtctgggg cgggccgggg ctgatgccaa aggtgtgggc  6420
aggccatggg agagccgggc tggggtgggc agggcctttg ggcagccgtg gactcaggcg  6480
cggcagtgga gaggcaggaa ggctgggtgg ggactgtcct gtgctggttg cctgcacgct  6540
cgaggccact tctgcttcct ctcctcctca aggaggttgt cctggcctta gagctgcgat  6600
cctagcggtt tgagcctcga gagctcctgc ccgccccact cctgcagcca gccaggagga  6660
gacgcctgcc attcatgagc ggggaccgag ggacgcagcc tgctgcctag cccctcctgg  6720
gcccttgggc cctttgaagg ccggcgtcca gcagagctgg ctggccaggc aggccggcat  6780
tatgggcatg actcagccca agcggaggtt aatgagcagc gcccagcaca gcagtgggac  6840
ttggggtcaa ggccaccccc gcctgagccc acaggcctgc ctggctacca actggctcag  6900
ctgccttccc gggcccccag accagagatg ccgggcccag gccgccactg cggcgggaca  6960
cacttcctgc tcctggcgtg gctgtccttc caaccctgtc tgtctcctgg ctccctggtg  7020
ggccggggcc ggcgggccag acaggcgctg ggaaaggtta ctccaggtca atgctccctt  7080
tatctcgcct cagcccctcc ccttcctcgt gcctggggtt gcagctgcct tgggccctgc  7140
tctctgcgac tcagtttcgg ttccccagtg cttcttggga ggagggggcac aatggcatcc  7200
atcccccgaa ggcctgtgtg tgctccctgg gtcaggtggc ctcttgccct gggaccttgt  7260
ctcactggct gtgcaccagc agagaagcag gcttgtcccc gaattccacg gagaggggca  7320
tcccgggtgt gggccagact gcagattcag agaaaaggcc cctggacttc agccaccacc  7380
ctggcttccc tctcctcttc tcccgcatgc tgggctgcag ggccttggca agcagctgca  7440
gccttgggcg aggcgcttgg cacattcccc gcagctacat tgtcagcctt ggctggcacc  7500
cctgccagct cccagcacga gtctggattg ccagggtgct tgcttcagga atgggagatc  7560
gggcttgcag ggagctcagc tgtgcaggcc gacctgggtg gcgggggcag aagagagatc  7620
actggttctt tgaaggcctt cgtccgggct agcttcagga agtagagaga ttactggttc  7680
tttgaagggc tagcttcagg aagtagcacg ttggccaaga gggtttgttg gccagggcag  7740
gagggcccgg tgtgcattca cggcctgtct gcataggcct cggctggaaa gctgtgtggg  7800
gtgagaggac cctcgggtag catgtggccc atggcagtcc cactggctga tgtccccgtg  7860
gacactggcc taggctcaga tcagggcaga agcagctgac tggctggagg gcacatagca  7920
gagtattctg tcctttctgg gattgccgcg aggaggctta ttgaaacgca catgcacacg  7980
atctcttgtt tgagaacaaa gtaaagctct cttgataagt ctaagcatca tttacaagaa  8040
tgtggttctt ctggcagctc tgccagtgtg gtccaaattc ccacactggt tgccaccatc  8100
aggctgtatg ggcttgggca ggtcactttg cctccctggg cttcagtgtt ctgtgtacag  8160
tgggcacgtg aatacacatg cagtgggatg tggggagaat caaatgcaga gacgtgaaag  8220
cacttggcaa acagtggcag gctaggcagc tgtcatcaga cggctgtggg gaggcaaggc  8280
tggggtgcgt gcccctggac tgagcccaga aattcacaac cccttggcta ccttgctggg  8340
agcacttccc aacacctccc atctccccg cctgtctgac tgctgctgcc acctcttccc  8400
tgcggctgtc cctttcccca cctgctggtg tcctgacata gtggtggcca gtgcaggaag  8460
ggggacagaa ggacagggga ggcctaccca ctgctgaggg agcaaggtcc aggctcagca  8520
gtggggacat ccactggggc gagtcctgta gggcccagct caggagcgca tcctcctggt  8580
ttcagtggga aaatgccatg caaatttctc accaaaagga agtgtgggaa agttgagggg  8640
aaagagggcg taaataggcc cagactgttg aaccgagttt ttcagaacca agagacaggg  8700
tttcactgtg ctgcccaggc tggggtgcag tggcgccatc actgcagctt caaactccag  8760
ggctcccgcg atcctcccac ctcagcctcc cgagtagctg ggactacagg tgtgtgccac  8820
cacacctggc taattttttt ttttaattat ttttggtaga gacagcatct cgccgtgttg  8880
gccaggctgg tctccaactc ctgggctcag gcaatcctcc cacctcagcc tctcaaagtg  8940
ctgggattgc aggtgtgagc tactgcactc agcccaagag cactgccttt tgctgtcctg  9000
```

-continued

```
cgctgctctt tgcttagttt aggggggggaa attagagctg atggatgatc tctccgagcc  9060
aggaggaggg ggctggcagg gagcccaaag aaatgggctc agcagaggac agaaacaagg  9120
tgactagaga gggagtggag aggggacggg agccgcactg tgacatcagc cagtccctta  9180
tacccccttta caccttgagt ttgagacctg gccccaccca atcgtaacct ctggctctcg  9240
gccttctgat ggccaccatg gcacagcgtg tgtgagtggc actgggagac cctgaccatc  9300
gcccccacgg gagctgcccc tgtgcatggc caggaagcct ctctgtgtct gtcacccccc  9360
gcaggtggag ctggccctgc tacagcgctc ctaccaggac ctggcctcgc agatcaacct  9420
catccttctg gaacgcctgt ggtatgttat gctggagcag ttcctcatga agtatgtgtg  9480
gagcgcctcg ggcctgctca tggtggctgt ccccatcatc actgccactg gctactcaga  9540
gtcaggtgag acccagggct ccaagaggat ccaggccagg ggcctgtccc ccataccgct  9600
gggtgctgag ctcacgaggg cccaactcag ccagcccgcc gcccacttct gctgccgggg  9660
ccaccgaggc cctgctgcca gccttgatgc tttcagaggt tgagctcgcc ttgcccctcc  9720
ttgttgcctt ttgccctgcg cgcacctcac gccctttgtt accactcaga caagcccagg  9780
actgcaagtc aggaacacta catgtcactt ctccaggcac agataccctc acccacctgt  9840
ccctgtcctc aacccaactg cgacttagag gtgggagaat gtgcggagta cctggagtga  9900
gccccttcat cactccagcc ttggtttcct cgccctgaaa cagctcttgc accctaaggt  9960
gttttagagg agtgggaagc ctgttctacc tgttatttta gtgataagat taaatgttta  10020
ggtttctgca ttcctgttgt ttttgtttgt ttgttttatt ttctttttgg cttttgaaac  10080
aggagtctga ctgtcgccca ggctggagtg cagtggcgcg accttggctc actgcagcct  10140
caacttccca ggctcaagtg gtcctcccac ttcagtctcc ccagtcgctg ggactacagg  10200
cacaagccgc cgtacctggc taattttaat atttttggta gagacagggt ttcgccatgt  10260
tgcccagact ggtctcgaac tcctggtcag gtgatcctcc cgcctcagcc tcccaaagtg  10320
ctgggattac aggtgtgagc tgccgcgccc ggcctgcatt cctgttttgt tcctctgccg  10380
gattgcaact tctgcatttg atttttagtc cattagtggt caccctttaa aaggtcaaca  10440
cgcagccggg cgcgggggct cccgcctggc atcccagcac tttgggaggg tgaggcgggc  10500
agatcacgag gtcaggaggt cgagaccatc ctggctaaca gggtgaaacc ccatctctac  10560
taaaaataca aaaatttagc cgggcgcggt ggcgggcgcc tatagtccca gctactcggg  10620
acgctgaggc agaagaatgg cgtgaacccg ggaggcggag ctggcagtga gcccagatag  10680
cgccactgca ctccagcctg ggcgaaagaa cgagacttcg tctcaaataa aaataaaaat  10740
aaaaaataaa agatcaacac gcatacttgt taggttaatc aatagctccg ccttctcctg  10800
gaccttagaa cgcagaagca gccccgtggg gcatggcatc atagcccagc caagagttgg  10860
atttgtacct agtttttcct ctttgctatc gccttatcca cacgtgttga aactcactcg  10920
catgtttgct gagttctgtg ctcaccattt cgttcctaca tctcaatttc tcttctatgt  10980
tctgttatct tcctccagat agacatgttt ttagtttttt gtttgtttgt tttttaactc  11040
acaactatgc tcaggacaaa cagtcatcag tgcttctagt tgtggttggt ttttaaaaaa  11100
ggttctttca gcaagggttt tgtcatggga aattcttgat tattttattg taattctttg  11160
tgttgtttag ttttttgttt gtttgtttgt tttttgtaga ggcaggttct cgctgtgttg  11220
cccaggctag tgtggaactc ctgggctcaa gcggtcctcc cgcattagcc tctcaaagtg  11280
ctgggattac agacgtgagc caccacaccc aggctgttgt cattcttgat tatttttgtt  11340
gaaaatgttt ctatttcacc cttattccca agctaaagtt gagttgcgca atggagtcta  11400
ggtggactgt tcttttctct cagccctttc acaatgtctc attgtctccc tgcttcttct  11460
gtagctgctg acaaatctgt agctgctaac aaattgtcct ccctgagtac cctgtgtttc  11520
tttttttctg ggtactttga tcactttctt tctttttggc attctgcagt ttcactatga  11580
catgtttagg tgtcagtttt tgttgattct gcttgagact tgttatatgt cctttgaata  11640
tttgagtttt tcaatcattc tggaagattc tcagctatta gcttttcaga tattgcctga  11700
ctctcattct tttttcctgt tcttctagaa ctggcagcca gtgctggact tctgactctc  11760
ttcgttgtgt ctttcggttt ctgtttactg tttcccatct cacactgtct gtgctgaatt  11820
ctggggatgc cctgaggcct tcctgtttgc tcattttcca gttcaccagt tttctctttg  11880
gccatgtcta attggaattt tgttcacatt tcagtggctg ttttgtaagt tctatttcat  11940
tctatttcaa ataggaattt gaaaatggac atttcctttt tcaagtagaa atgtcaggct  12000
gtttctgtgt cttatttgct catctttttg actgctcctt ttatactgtg tatcaggtta  12060
gtcatactta ccccaccgtc tctatctgat ggtttggtta gcttcagttc ttgggagtat  12120
cattcgcctg tcttctgtct gctggtcttc actcatggtg gatcatttcc ttgtgggttt  12180
tgcaacagaa cttctatggg gattggtgtg gcctcaatgg agggtgtaag tccaaatgtc  12240
cttctgtttt ggccaagcac tccagggtaa gcagttggag gccattagtt agtgcggagg  12300
ggatggttcc tgaattgaga ggtggtttca tttgaattca tttgaactcc aggcacattg  12360
ttacaaattt tcagaggagg ctttttgttc attgggcata gagcccaggc taagcaagga  12420
aagcttcctg gtctttgccc tgcctgcctc tggggctatc aaaggatcac ctggctgtct  12480
gcttctcttt gctcccagaa gtttcccttg ctttccgtca agcttggctc tgctcgaaat  12540
agtgtcgtag tttacccagt ttggtgggaa gagggttttc gatttataaa cagaagtctg  12600
attctctccc tgttcctgtt tccacctcgg ggcttccatg ccctcaactg tctgtgtcat  12660
cctctgggtg actcaccaag aggaaggatc taattcgggg actgcacatc aagggcagcc  12720
ttgatgctgg cgtaggtgcc cagcccagtc agcgcaccta gccccgggca ccgagacagc  12780
ccgcgagaca gcacctgcag ccgcttcgct ccatggctgc cattggtcac atcgggctgc  12840
tccctgccct gaaggcttag gacttttctg agcctctgct gtgccaggct ttgtgggctc  12900
ctggccctgc tctggtggtc ctcagagcca gcagcctttg aaggctgtga agcattccct  12960
ttcccctggc ttgataggct ctgtcctgtg gccgtctgtt tttttttgga gggggagctt  13020
ttgagatgga gtctcactct gtctcccagg ctggagtgca gtggcacgat cttggctcac  13080
tgcaacctcc atctcccggg ttcaagtgat tctcctgcct cagcctccca agtagctggg  13140
actacaggta cacgccacca tgcctggcta atttttgtgt ttttagtaga gatggggttt  13200
cgccatgttg gtcaggctgg tcttgaactc ctgacctcaa gtgatccacc tgcctcggcc  13260
tcccaaagtg ctgggattat aggtgtgagc cactgtgcct ggtcctgtgg ccttcttatt  13320
tccccaaatg ccaggcctgc tctgtcttgg ggcctgtgcc aggagcactc tttcctctgc  13380
tgccccatgg cgcagccccc ctaggcaagg cccggcctgc ccaccgccac ctttcctgtc  13440
tccttccctg ccccactgct ctcccaagca ctcgacaccc cgtcagtggc gcttttctct  13500
ctccctgcca tggactgcaa gctccatggg gtcagggatt tttgtctgtt ttgtccctgc  13560
tgtgtcccct gcatcgggtg gctagtgagg gctccaggtg cttcaaggag gtggagcgca  13620
ctgggtggga aggcaggctc ttaccggttg gaagatttag ataagctttg ctgggctggt  13680
gtgcaaggca ggtgggctca ggagatgggc agggcctgtg gctcccactc cagccctgag  13740
```

-continued

```
gccttgctct gtccagctct ggggccctgg ccttattcac ccaaggctcc aagagaacct  13800
gcagaaggca gctggttcta cgccaggatg ccctgggcac aaagacttgc agacccttcc  13860
ctttgtccac agcgactgtc cagctctcag aacacctggg gaggagggct gtgtccttga  13920
gagcaccgtg ggaaggaagg tccaaggcct tcgaccttta ggattcacat ccccgccccg  13980
ccagcccaat ctagttccct ggtttcccgg gccaggcccc tttccaccct gcatggccct  14040
gagcggatac tgcgttccgt gtcttccccc agcccccagc caatgatccc tgaggcttcc  14100
ccctcaggat cacacccacc cctggataca gtcctcgggt ccttcacagg acattcccac  14160
cacttcagcc acaccccagc accctcagag gcggccttcg cccttgctcc ccacctctgc  14220
tcctgtgggg aatctaagga tcaagaaact gagagtcaag gccattgatg agggtcaggg  14280
gtgctgccac ggggcctaga gtgtgacaga aaagcaaatt aagacaggag cagctcctgg  14340
gagaagcaga caccaaacaa tacggctgct ggcccagagg tcaaaaacca tggcctagag  14400
ggggcggtca ggaagtggga cattaggccg ggcgtggtgg cccatgcctg caatcccagc  14460
atctttggag gccaaggcaa gtggatcacc tgagttcagg agtttgagac cagcctggcc  14520
aacatggtga gacttcgtct ctactaaaaa tacaaaaaaa attcgctggg cttggtggcg  14580
ggtgcctgta atcccagcta ctcgggaggc tgaggcacaa gaatcccttg aacctgggga  14640
ggcagaggtt gcagtgagcc aagatcacac cactgcactc cagcctgggc aacagagcaa  14700
gactccatct caaaaaaaag aaaagaaaaa aaaaagaaag ttggcgtttc aaagccaaac  14760
agctctgggc gttggatgac aaagttcaga tgtgccccag gaggggcgac atcagtggtg  14820
caggacagag ggccggtgga aggagctggc tgtacgtaga aacaaaacca gatgcctact  14880
ggtgcattta aaaatcaacg ttattgagac gtaattaaca tactatacaa ttcttccttt  14940
tccatgtaca gtttaaattc attcacagag ttgtgcagcc atcatcacta actccagaat  15000
gttttatttt tattttatcc cccaaagaaa ccccagaccc atgaacagtc actcctcatt  15060
ccctctctcc agcccctggc acccactcat ctgcttcctg tctctgtgga tttgcctatc  15120
tggacatgtc ctagaaatgg aatcatgtgc tctgtggcat tttgtgacta gcttccttca  15180
ctgagcatca tggtttcaag attcgtccat gtcataagat gaatcagtcc ttcattcctt  15240
ttcatggctg aataatattc cattgtgtgc atagaccaca atttctttat ccattcatcc  15300
cttgatggac attttgggtt tcttcatgtt ttggctattg tgaataacac tgctgtgaac  15360
atccatggac aagtctctat gtgtgcagat attttcgttt ctcctgggtg tgtagctagg  15420
agtagaattg ccaggtcaca tggtaactgg acgtttcact ttttgaggag ctgcgagact  15480
gttctccaca gtggctgccc cattttacct tcccgccagc agtgttggag ggttccacct  15540
tttcatcgtg gctagcactg gttatcatct cctttgtatt ctagccacct agtgggtgtg  15600
aggcagtatc tcttggtggt tttgatttgc atttccctga tgactaatga cgctgagcct  15660
cttttgatgt gttgagtggc catttgtatg tcttctttgg agaaatgtct gttcacgtcc  15720
ttcgcccatg tgtgatcggg ttatctctgt cgctgagttg taaaagctct ttgtatattc  15780
tggatactgc accctcatca gatgtgtggt tcaccagtcc agagttttct cccagtctgt  15840
aggttgtctt tttcactgtc tcgatattgt cctttggtgc acaaaagtgt tgagttgaat  15900
gaggttcagt tgatctgttt ttctcttgtt gctcatgctt ttggtgtcct agtgaaggaa  15960
ctattgccat atccaaggtc gtgaagtttt atcccatttt cttctgagag tttcatactt  16020
tgggccacac tacacatcag cctgtgatgt gctctgggtt ggtttgtctg tatggtgtga  16080
ggggtccctc tcctgcacat agagagaaag agagagagag ctggttgccc cggcaccatt  16140
tgcagaagag cctcgccttt ctctccagcg gctcattttt gactttccgc tgtctctgcc  16200
ctgcccctcc ccgccccgcc acccacccct ctggggcttt gcagatgcag aggccgtgaa  16260
gaaggcagcc ttggaaaaga aggaggagga gctggtgagc gagcgcacag aagccttcac  16320
tattgcccgc aacctcctga cagcggctgc agatgccatt gagcggatca tgtcgtcgta  16380
caaggaggta cccctggccc agccccaccc ttgccatcct tgccatgctt ctctccctgc  16440
aactggcagg ggctgagcca gggtcaccct ccctcaggtg acggagctgg ctggctacac  16500
agcccgggtg cacgagatgt tccaggtatt tgaagatgtt cagcgctgtc acttcaagag  16560
gcccagggag ctagaggacg ctcaggcggg gtctgggacc ataggccggt ctggtgtccg  16620
tgtggagggc cccctgaaga tccgaggtaa ggctgtcccc tccctatgag tgaccccgcc  16680
cctgctgctg ctgcaggtgc tgacctgctg ccccagctcc tcctattccc gctccctcac  16740
tcagggacct ccatgtgctt ctggcccatc ccagtccacc caggacggga gggctgccgg  16800
gcagggtctt tgaggacttc ggcctggtcg agctgggccc ctggagggtt tcctgcagag  16860
aggtgctggt ccgcccgcct tccttcccag acagtagctg ccggccaccg tactgactcg  16920
ccctttgagg gcctcagcct ggattattca ttcaaaacaa gggggatgtg gtcccctcac  16980
ccatgcagga cagcaagaga aagttccagt cagtgtgcca gctgctggct gccacgggag  17040
gcaggtgctg cagaagggag tggcggccca gggcactgta ttagacactg gggggaagagt  17100
tcagcttgtt ggaagacctg gctgtgttcc ctagggaccc tggaccacag gctgctggtc  17160
aggaaccagc tggcatgctg ccagggatgg gaatgagggc gtgcagccag gggcacgcag  17220
actccccaga atgcagaggg gtcgccacca ctccctctcc accccagccc cgctgtgctg  17280
tctctgcagg ccaggtggtg gatgtggaac aggggatcat ctgcgagaac atccccatcg  17340
tcacgccctc aggagaggtg gtggtggcca gcctcaacat cagggtaggt ccagcgggga  17400
gggcgccagc cacgcacata tgcaagcctc agcccttggc ttcccgcctg tctgtgctgg  17460
caacagccat tgtccctaga tgtacgtggc aggtgggcca aggtcaaggt gagagaccaa  17520
cgtgtctctg actgttcatc ctggggcaac agaggcaggg ctcataaaag agactagtga  17580
taccaggatt gaccaaggtt caccccggcg ttcctggccc tatcatctga tgccaactcc  17640
ccacactcct aagaaagcca agacccgggt gggggggctc tggttcaaac cttgccgctc  17700
gacctccctc ggaaggccac agcaaggaat ccacagatca cctgtgtccc cagccagggg  17760
tttggacagg gctggggagt aatggagtga gggggagact ggggtggagg gacaggtaga  17820
gaagtgacaa ggaatcactc attcattcac tcatttaacc aatgtgccct gaactctgag  17880
ccgggcacca gaaacccgag gtaaatcagg agacctgcac tcagggagtc ttcactgtgg  17940
aggggcacta aagtgttaca aagggtctcc aggtagacag ctgttcaagg gacagtgggg  18000
gtcacaagaa gagtggtcag agtccctggg ggtggtgggg gtgggatgaa gccttgccca  18060
ggagttgctg tgagcgagtg ggcaggcagc tgagggtaga ggagtgaggg gccgtgggcc  18120
tgaggggcag gtcacgcagg aggaagcaga gaggaggggc atgccaggga ggagggggcc  18180
ggcacaggtg gttacccctc accgctcgca gcggcccctc ctaggatgtc gggggagctg  18240
atcaccagtg agtccaagga aggtggtttc caggctggcc ccgggcagca caagcaggca  18300
ggggcagcgg gcaagctcat ggggcccctg cgcgcagggc cacatatgct cagggagccg  18360
ggtatgcgag atggggcaag gcccaggccc caccccttcag gaggggacag tcaggtggct  18420
tcattagcat cctgtggctg cggtcacaaa gcgttacaaa ctttgagtgg ctttcccagc  18480
```

-continued

```
agagatggcc tctctcccgg ctcggggaat agcagtccga gaggaaggcg caggcagggc  18540
gggcttctgc caaggaccga gaaggtgcct ccgctcgggg cctctgtccc agcttctgct  18600
ctgctgccca tctgcgggct tccctggctt ctgccacggc aggtcggcct cagcctctgt  18660
ctccacacgg cgctctccct ctgggtgtgt ccgtgtctcc gtctcccctt tctgtcagga  18720
cacaggtcac actgcattag ggcccacccc tctgcagaat gacctcatgc agacctaact  18780
catcacgtcc gcaatgaccc tgtttccaaa taagctcaca ctccgaggta gtggggatta  18840
gggttcccac ataggaattt cagaggacag agttccaccc atgacactgc ctgaggtaag  18900
ctaaagacca cggcctcaag tcttcccagg agccccgtgt agcattgttg ttgttaccgt  18960
gaacttcact gactccaggc ccctggcctc ctccctgcac acagcccgcc tccagcctgg  19020
ccggcatttt cccaaagtag gcatttccta gctccagcga ggaccatgga gtcagtgaat  19080
tgaggagcct gaggtccatg atgcagagcc caggggccac tgtggcatct ctgggccact  19140
ctggcacctg gggaggcagt ggggtctgta ctgtcagtct agagacataa agaaagtgct  19200
ttttgggccg ggcgtggtcg ctcatgcctg tcatcccagc actttgggag gccgaggtgg  19260
gcagatcgct taagcccagg agttcaagac cagcctgggc aacatggcaa accccgtctc  19320
tacagaaatt tttaaaaata cacaaataag ccaagtgtgg tggcggtgcc tgtagttcta  19380
gccacttgaa aaaaaaggct aaagtgagag ggtctcttga gcccaggagg ttgagcctgc  19440
agtgagccat gatcccacca ctgcactcca gcctgggcaa cagagcaagg ccccgtctca  19500
aaaagaaaag aaagaaactg ccttttgtcc ccagtgactc aggaggccaa ggtgagagag  19560
tcgcttgagg ccaagagttt gagaccagcc tgagtaacat agcaagaccc tgtctctaaa  19620
acaacattta aaaattagcc aggcatggtg gcgtgcatct gtaggcccag ctactcagga  19680
ggctgaggtg ggaggatcac ttgagcccag gagttggaga ctgcggtgag ctgtgatcat  19740
accgctgcac tccagcctgg gcaacagagt gaggtctcgt ctcttgaaaa caaagtgcct  19800
ttcagggcag ttccttaaag ggggctgaca gttgaccctg cacttggatt cctggtgaag  19860
tgggagtcgg atgggactga ggacggcgct ggctgtgttg gaacacacct actcattcag  19920
ctgtggcaga ataggccctt cctcttgtgc tggcaccatg ttctccaggc gtgtcagggc  19980
ctgaggactg ggccggggct tgtccattcc tgtgtcctgg gccaggcatt tagcgagagc  20040
caaatttagc tagggctgtg gacgctggac cccatccccc aggccctgct gtcccttatc  20100
aagagatcaa gaatggcctg cgtgctggcc tcgggcattg ggagcctctc aaggctggtc  20160
aggaggccat agggtacggg aaggggcctg cgctctctgg cgtcagcggc tgttgcccct  20220
gcaggtggag gaaggcatgc atctgctcat cacaggcccc aatggctgcg gcaagagctc  20280
cctgttccgg atcctgggtg ggctctggcc cacgtacggt ggtgtgctct acaagccccc  20340
accccagcgc atgttctaca tcccgcagag gtaaggaagc ccgtgcgcct ctcctccacc  20400
tcttcctgcc tgtgcgctca cacatggctt cctgcagagg cccaggaagt ggtgaagagt  20460
cagcacctca ggagaggaca ctgaggcact gtccccagag ccagagacgg gctgtggttc  20520
ctgctccctc caaacccgcc cgatccactg ccctgttttg gatctgtgtg gggtgtgtgc  20580
acgggcggcg atgtgagcgt gtggatgcgt gtgagcgtgg catgtggaca ctgcctggga  20640
ggcgcagagt atcttggggg aggcagagcc ggcccttccc tccgtggaca cccagctttc  20700
ccacaggccc tacatgtctg tgggctccct gcgtgaccag gtgatctacc cggactcagt  20760
ggaggacatg caaaggaagg gctactcgga gcaggacctg gaagccatcc tggacgtcgt  20820
gcacctgcac cacatcctgc agcgggaggg aggtaggagg cctggggctg gcagccaccc  20880
tttgtcccac cctggcctct cccttggcct ccagggagtg aagattacct caacatccag  20940
agtctaaagt gccaggtgcc acggggcggg gcagaggctg ctaccaggga ggaccaacac  21000
cacacagatg gccccaggtg ctctagggaa gggggcacct agcagggatg tgcacctcac  21060
tgggggaccc aggataccct ctcccagaga aaagaggtct gagctgagcc ctgcagaatg  21120
ctgagtggtt accccgtccg gaagccaggg gcagcagggc ggagtgcgtt ccgaaggctt  21180
ggtggtgcga gaggctggct cacagagggc cctcgggacc aggcgggagc ctaggctttc  21240
cctgagcagg atcagacgct cttggaagga ccatggggtg gtgggcaggg gcagcctggg  21300
aggggcaggc acatgtgtgc agtgatggct actgtcaaga ggtttgtgca gacgcttgga  21360
gggggctggg gccagcagag tcaggtggat tcagagatga gttcactgaa aaggaggcca  21420
gactgagctg ttgtcttgtc ctgggcttat caaggaatac tgcttgtcca cagtgtctgt  21480
cgggccggaa gagcggagga ggagaggggg ctgcagctac agggacacag tagatggagt  21540
gttcagttct gtctttgaat tctgagcctc tgggttctgc ttccagcctg cactgctggg  21600
tgcgagatgg ccctgggcaa ggacctcgcc ttgctggggc tccccttcac ggttcaaggg  21660
cacgggcacc aagccctccc tcggtggcaa catgagaaga agtggctcct gcaggaaatg  21720
gccggggtgt tgtcacctgc ctgtggagga agcggggaca caggtggcaa tggcagtgga  21780
gcagcccctg gcccggccct gcctcttgct cctgctgccc tcagcctggg agcacgtggc  21840
ccctcccgcc tctgtggcag cctgaatgcc cagggcctgt ggccggccag catgagccat  21900
taggatggag ttgagctgcg aggaacagaa cgggcctccc cgcaatagtg gctaagatca  21960
tctgtgagtt tatcctactg agctgttagg tcccaagaga gccaggccac ggttgccagg  22020
gctggccctg ctctgtgaag gccccagggc tcgaggattt tctaccaggt cactctgctg  22080
tgtttggcct ccgttcccaa agtcacctca tgatccagga gggctgctgc agccctcaca  22140
tcatgtccca ggctgtagga tggaggaagt agaagggaag gggcaaaagg tatgtgcctt  22200
cttttaagga aggttccaga agccgccata ttgaatactt acagttatat ctcattggcc  22260
acaacttagt ctcatgctca cacctcatca caaggccacc tgggaagcgt aatctctact  22320
ctgggtggcc atatgccctg ttgccacttc tagccctggg ccgctgggga aggcagcatg  22380
ggcgagaaga caggaagggc cgcttctgcc gcagcgcccc gacctaatgg agcagccggc  22440
tcacctgctc gttcaagcag cccactcgag ccttgccaaa gtgctgacac ggggcagtga  22500
caggaggccc aacccctgtg ggtgacaagc ccccggtctg gggagagcac tcaggccgct  22560
ctggagctct gtgccaagga actgtatggg tgccctgggg ctgccataaa ccgcagggat  22620
ggattgtctc ctagatccag cagtccgaga tccaggtgcc agcagggtgg gctccttccg  22680
ggtgccatga cagaaggatg tgttccaggc ctctgtcctc ggctcgcaga tggtccactt  22740
ctccctgtat atcttcacct catgttcccc tgtgcatgtc ttctgcccac acacccccctt  22800
tttatgagga cacagtcata ttgaattagg gtccactctg atgacctcat cttagtgtga  22860
tcacctctgc gaaggccctg tctccaaata aggtcacact gaagtgttgg ggcttggact  22920
ccaccgtatc tcttctgggg gaaggcacga ttccagtccc cactcctcca tgattaatgc  22980
ctgtcagaca gacaaggacg cagaggcaca ggggccctgt cgtcacagct agctcattcc  23040
cgcagctccc ccagctcccc ggctggcccc cgggtctggg tgctggtgga actgagccaa  23100
gaccattgcc cccgcctagg ttgggaggct atgtgtgact ggaaggacgt cctgtcgggt  23160
ggcgagaagc agagaatcgg catggcccgc atgttctacc acaggtgagc actccgggcc  23220
```

```
ggcaggctcc ctggggtccc ctggaagggg aagtagcagc tgtggggagg cctgggctca  23280
gtggagcctg agccgggctg gggtgttggg ccctggaggg tgcacagact ctcctctcgg  23340
cccggacccc caggcccaag tacgccctcc tggatgaatg caccagcgcc gtgagcatcg  23400
acgtggaagg caagatcttc caggcggcca aggacgcggg cattgccctg ctctccatca  23460
cccaccggcc ctccctgtgg taggtgccct gtctccctgc ctggggtcgg tgggagtggc  23520
tgcctgaggg gaggaggtgg cctggcgggc ccggcagcag caggcggctg tcatcagcag  23580
cccccgtgcc gtgcccctga ccctgtccct ctcctggcca ggaaatacca cacacacttg  23640
ctacagttcg atggggaggg cggctggaag ttcgagaagc tggactcagc tgcccgcctg  23700
agcctgacgg aggagaagca gcggctggag cagcagctgg cgggcattcc caagatgcag  23760
cggcgcctcc aggagctctg ccagatcctg ggcgaggccg tggccccagc gcatgtgccg  23820
gcacctagcc cgcaaggccc tggtggcctc cagggtgcct ccacctgaca caaccgtccc  23880
cggcccctgc cccgccccca agctcggatc acatgaagga gacagcagca cccacccatg  23940
cacgcacccc gcccctgcat gcctggcccc tcctcctaga aaacccttcc cgccctcggg  24000
aaagtagatg tggagggtgg cgccctgcgt aaccctcgcc ctgtccctcc cactccctgg  24060
gggcgctgtt ccacagtgac tgggccctgt ccagggcagt gagtcctcta ctttgctccg  24120
tggaggaagc tggggtacaa ggggcccagt gctggccaca cagcagcgca gccgagcccc  24180
aggagcccgt caggccacag cccctggcac tgcaggtggc ctccctccag agactcgagt  24240
ccccatgatt ccctcctcgt cagtctctca aagaccccat ggtccatccc ctgagggtgg  24300
tcagccaagg ctcccgttcc gtgggatgcc ataaaagccg cccagtggga cccacagtca  24360
cacagagcgc ctcacctgca tcctctcccc cacaagagcc ccaaagatcc cacgggagag  24420
gggagaggga cgcacagcac tgcctgccaa gcgagaatgc aggccccgcc ccctcggccc  24480
ctcaccacct ctttctacag cctaatttat tggattccct attcgtagcc atctccgtgg  24540
ccaatgtgac taccgtgcca gcagcggggg cggcccagcc tctgagtccc gtggggcccc  24600
ggctcccacc ggtgccaaac ccagcccctg cggccgtcac cccgccagcc tacactgcca  24660
gccgccaccg gggcacacgg gcctctgctt gccagccagg agtgcggaca ccatgttccc  24720
agctcagtgc caaagagggg tcaccagggg gagctgtctg cggagccagc gcctgcccga  24780
gagagacccc accgccaccg tgtgcctttc ccgggccctc agccctcggg ccgggcacca  24840
cccccagtcc ccccagtaaa agcctccact ggcaaatgca gtccttcctc cctgcctcag  24900
agcctggtgg tgtctgctgt gggtctcgag gagagatgga ggagagggag tgggttgcct  24960
gtgggggaaa gagtgagttt gggaaaggag tgggcctgac ccccaagccc ctccgagggg  25020
gaaagtcacc agaagacatg gtccagcatg ccctccgccg agcctcacgc caatgctctt  25080
aggattcctg tgacggtggc ggggcggaac ctgcaacaac attgcacaga aatactggct  25140
gagcccaaat aggactaggg gaggggatca tgctggtccc tgtgggagga gcacgaaggc  25200
aagagaaggg atgtctaagc tgccacacag ggtgctgctg gcccttctag ggagaggcgg  25260
ccacttgtgc aggggcctgg ggggaactgg gagcacagcg caggtgttc gtgctgcatg  25320
caggggaagg gagggcaggg gaagggaggg ctgcggccgg cgggccttgg aggccacact  25380
acagagacag gacttagccc agaggccacc gaggagcttt cagcaacagg gaagcagtgt  25440
cgagtactgc aggccacgtg gctgcatgtg agggtggctg gtgggaatag ggtgcggcag  25500
cccatctggc ctcagaggca cgagaactga gaacagctgt gcggccatac ctttatgcat  25560
ggatggccac agcctcccaa aggtggggca gcctgagtgt tcatcaacag acaaatggac  25620
aaacagcctg tccataaggc acagtgccat tctgccataa cacgacagat agacctcaaa  25680
gagttcgtgc tgggtgaaag aagccagaca caaatgtcca gaataggctc atcgggacag  25740
aaagcagaca agtgggtgtc aggggctggg gcaggggaag gaaaatgtgg cggggggagt  25800
cctttttaaa aaattttgta tttatttttt atttttttaat gagacagaca gggtctcacc  25860
ctgtcaccca ggctggagtg cagtggcgca gtcataactc actgcagcct tgatctcccg  25920
ggctcaagca atcccgcccc agcctcctga gtagctggaa ccacaggcgt gtgccaccat  25980
accctgctaa ttttgtgatt tttttttttt ggagacagga tctcactatg ttgcccaggc  26040
tggtctcaaa ctgctgaact caagcgatcg tcctgcctca gcctcccaca gtgctggatt  26100
acaggcatga gccaccacac ccagcctcgg gtttcttttt atttcgaaga aaatgttctc  26160
gaactataga gcatactaaa tgccactgaa ttatgcactt taaagggatt gattgtatat  26220
tttgtgaata tcgcctcaaa aacagatgat tgatggataa attgatacat agatatatag  26280
atatatagac atgattgata tagatgattg attgatagat gatggatgat tcataggtga  26340
taagtgatag ataaaataca tgatagatac atggatagac agatgaatag agagagatga  26400
tagatggttt taaaagtttt tttagagaca agatctcact atcttgccca gtctggactc  26460
gatctgctag catcaagcag ccctcctacc tcagcctcct gagttactgg gactacaggc  26520
acatgctact gtgcctggtg atagataaat gattgaaaga tagacatgat agaggcataa  26580
atgatagata gatggataga catgataaaa ggaagataca tgggatagat caatgattga  26640
ttatataagt aaatgatata aattgataga ttattgatta tagattaata ggcggatagt  26700
tgattgatag atgattgatc gattgattga ttgattgatg gagagagaca gagaagcaag  26760
cacagccatt gcagccaccc agacaagaca tgctgaggcc tgaagttcca gaaggttcga  26820
gcagttggaa gaactcaaca ggcatggggg cagcttcttc agggagtgga gggggcagca  26880
aggtaccact gggtt                                                   26895
```

```
SEQ ID NO: 9            moltype = DNA  length = 3697
FEATURE                 Location/Qualifiers
misc_feature            1..3697
                        note = Genbank Accession No. NM_000033.3
source                  1..3697
                        mol_type = genomic DNA
                        organism = Homo sapiens
SEQUENCE: 9
gccaggctgc ggagcggacg gacgcgcctg gtgccccggg gaggggcgcc accgggggag  60
gaggaggagg agaaggtgga gaggaagaga cgcccccctct gcccgagacc tctcaaggcc  120
ctgacctcag gggccagggc actgacagga caggagagcc aagttcctcc acttgggctg  180
cccgaagagg ccgcgaccct ggagggccct gagcccaccg caccaggggc cccagcacca  240
ccccgggggc ctaaagcgac agtctcaggg gccatcgcaa ggtttccagt tgcctagaca  300
acaggcccag ggtcagagca acaatccttc cagccacctg cctcaactgc tgccccaggc  360
accagcccca gtccctacgc ggcagccagc ccaggtgaca tgccggtgct ctccaggccc  420
cggccctggc gggggaacac gctgaagcgc acggccgtgc tcctggccct cgcggcctat  480
```

-continued

```
ggagcccaca aagtctaccc cttggtgcgc cagtgcctgg ccccggccag gggtcttcag  540
gcgcccgccg gggagcccac gcaggaggcc tccggggtcg cggcggccaa agctggcatg  600
aaccgggtat tcctgcagcg gctcctgtgg ctcctgcggc tgctgttccc ccgggtcctg  660
tgccgggaga cggggctgct ggccctgcac tcggccgcct tggtgagccg caccttcctg  720
tcggtgtatg tggcccgcct ggacggaagg ctggcccgct gcatcgtccg caaggacccg  780
cgggcttttg gctggcagct gctgcagtgg ctcctcatcg ccctccctgc taccttcgtc  840
aacagtgcca tccgttacct ggagggccaa ctggccctgt cgttccgcag ccgtctggtg  900
gcccacgcct accgcctcta cttctcccag cagacctact accgggtcag caacatggac  960
gggcggcttc gcaaccctga ccagtctctg acggaggacg tggtggcctt tgcggcctct  1020
gtggcccacc tctactccaa cctgaccaag ccactcctgg acgtggctgt gacttcctac  1080
accctgcttc gggcggcccg ctcccgtgga gccggcacag cctggccctc ggccatcgcc  1140
ggcctcgtgg tgttcctcac ggccaacgtg ctgcgggcct tctcgcccaa gttcggggag  1200
ctggtggcag aggaggcgcg gcggaagggg gagctgcgct acatgcactc gcgtgtggtg  1260
gccaactcgg aggagatcgc cttctatggg ggccatgagg tggagctggc cctgctacag  1320
cgctcctacc aggacctggc ctcgcagatc aacctcatcc ttctggaacg cctgtggtat  1380
gttatgctgg agcagttcct catgaagtat gtgtggagcg cctcgggcct gctcatggtg  1440
gctgtcccca tcatcactgc cactggctac tcagagtcag atgcagaggc cgtgaagaag  1500
gcagccttgg aaaagaagga ggaggagctg gtgagcgagc gcacagaagc cttcactatt  1560
gcccgcaacc tcctgacagc ggctgcagat gccattgagc ggatcatgtc gtcgtacaag  1620
gaggtgacgg agctggctgg ctacacagcc cgggtgcacg agatgttcca ggtatttgaa  1680
gatgttcagc gctgtcactt caagaggccc agggagctag aggacgctca ggcggggtct  1740
gggaccatag gccggtctgg tgtccgtgtg gagggccccc tgaagatccg aggccaggtg  1800
gtggatgtgg aacaggggat catctgcgag aacatcccca tcgtcacgcc ctcaggagag  1860
gtggtggtgg ccagcctcaa catcagggtg gaggaaggca tgcatctgct catcacaggc  1920
cccaatggct gcggcaagag ctccctgttc cggatcctgg gtgggctctg gcccacgtac  1980
ggtggtgtgc tctacaagcc cccaccccag cgcatgttct acatcccgca gaggccctac  2040
atgtctgtgg gctccctgcg tgaccaggtg atctacccgg actcagtgga ggacatgcaa  2100
aggaagggct actcggagca ggacctggaa gccatcctgg acgtcgtgca cctgcaccac  2160
atcctgcagc gggagggagg ttgggaggct atgtgtgact ggaaggacgt cctgtcgggt  2220
ggcgagaagc agagaatcgg catggcccgc atgttctacc acaggcccaa gtacgccctc  2280
ctggatgaat gcaccagcgc cgtgagcatc gacgtggaag gcaagatctt ccaggcggcc  2340
aaggacgcgg gcattgccct gctctccatc acccaccggc cctccctgtg gaaataccac  2400
acacacttgc tacagttcga tggggagggc ggctggaagt tcgagaagct ggactcagct  2460
gcccgcctga gcctgacgga ggagaagcag cggctggagc agcagctggc gggcattccc  2520
aagatgcagc ggcgcctcca ggagctctgc cagatcctgg gcgaggccgt ggccccagcg  2580
catgtgccgg cacctagccc gcaaggccct ggtggcctcc agggtgcctc cacctgacac  2640
aaccgtcccc ggcccctgcc ccgcccccaa gctcggatca catgaaggag acagcagcac  2700
ccacccatgc acgcaccccg cccctgcatg cctggcccct cctcctagaa aacccttccc  2760
gccctcggga aagtagatgt ggagggtggc gccctgcgta accctcgccc tgtccctccc  2820
actccctggg ggcgctgttc cacagtgact gggccctgtc cagggcagtg agtcctctac  2880
tttgctccgt ggaggaagct ggggtacaag ggcccagtg ctggccacac agcagcgcag  2940
ccgagcccca ggagcccgtc aggccacagc ccctggcact gcaggtggcc tccctccaga  3000
gactcgagtc cccatgattc cctcctcgtc agtctctcaa agaccccatg gtccatcccc  3060
tgagggtggt cagccaaggc tcccgttccg tgggatgcca taaaagccgc ccagtgggac  3120
ccacagtcac acagagcgcc tcacctgcat cctctccccc acaagagccc caaagatccc  3180
acgggagagg ggagagggac gcacagcact gcctgccaag cgagaatgca ggccccgccc  3240
cctcggcccc tcaccacctc tttctacagc ctaatttatt ggattcccta ttcgtagcca  3300
tctccgtggc caatgtgact accgtgccag cagcgggggc ggcccagcct ctgagtcccg  3360
tggggccccg gctcccaccg gtgccaaacc cagcccctgc ggccgtcacc ccgccagcct  3420
acactgccag ccgccaccgg ggcacacggg cctctgcttg ccagccagga gtgcggacac  3480
catgttccca gctcagtgcc aaagaggggt caccaggggg agctgtctgc ggagccagcg  3540
cctgcccgag agagacccca ccgccaccgt gtgcctttcc cgggccctca gccctcgggc  3600
cgggcaccac ccccagtccc cccagtaaaa gcctccactg gcaaatgcag tccttcctcc  3660
ctgcaaaaaa aaaaaaaaaa aaaaaaaaaa aaaaaaa                          3697

SEQ ID NO: 10          moltype = AA  length = 745
FEATURE                Location/Qualifiers
REGION                 1..745
                       note = MISC_FEATURE - Genbank Accession No NP_000024.2
source                 1..745
                       mol_type = protein
                       organism = Homo sapiens
SEQUENCE: 10
MPVLSRPRPW RGNTLKRTAV LLALAAYGAH KVYPLVRQCL APARGLQAPA GEPTQEASGV  60
AAAKAGMNRV FLQRLLWLLR LLFPRVLCRE TGLLALHSAA LVSRTFLSVY VARLDGRLAR  120
CIVRKDPRAF GWQLLQWLLI ALPATFVNSA IRYLEGQLAL SFRSRLVAHA YRLYFSQQTY  180
YRVSNMDGRL RNPDQSLTED VVAFAASVAH LYSNLTKPLL DVAVTSYTLL RAARSRGAGT  240
AWPSAIAGLV VFLTANVLRA FSPKFGELVA EEARRKGELR YMHSRVVANS EEIAFYGGHE  300
VELALLQRSY QDLASQINLI LLERLWYVML EQFLMKYVWS ASGLLMVAVP IITATGYSES  360
DAEAVKKAAL EKKEEELVSE RTEAFTIARN LLTAAADAIE RIMSSYKEVT ELAGYTARVH  420
EMFQVFEDVQ RCHFKRPREL EDAQAGSGTI GRSGVRVEGP LKIRGQVVDV EQGIICENIP  480
IVTPSGEVVV ASLNIRVEEG MHLLITGPNG CGKSSLFRIL GGLWPTYGGV LYKPPPQRMF  540
YIPQRPYMSV GSLRDQVIYP DSVEDMQRKG YSEQDLEAIL DVVHLHHILQ REGGWEAMCD  600
WKDVLSGGEK QRIGMARMFY HRPKYALLDE CTSAVSIDVE GKIFQAAKDA GIALLSITHR  660
PSLWKYHTHL LQFDGEGGWK FEKLDSAARL SLTEEKQRLE QQLAGIPKMQ RRLQELCQIL  720
GEAVAPAHVP APSPQGPGGL QGAST                                      745
```